(12) United States Patent
Chen et al.

(10) Patent No.: US 9,533,045 B2
(45) Date of Patent: Jan. 3, 2017

(54) PHOTOTHERMAL THERAPY USING MAGNETIC NANOPARTICLES

(71) Applicant: THE REGENTS OF THE UNIVERSITY OF MICHIGAN, Ann Arbor, MI (US)

(72) Inventors: Hongwei Chen, Ann Arbor, MI (US); Duxin Sun, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 74 days.

(21) Appl. No.: 14/457,650

(22) Filed: Aug. 12, 2014

(65) Prior Publication Data

US 2015/0051534 A1 Feb. 19, 2015

Related U.S. Application Data

(60) Provisional application No. 61/865,840, filed on Aug. 14, 2013.

(51) Int. Cl.
*A61K 41/00* (2006.01)
*A61K 33/26* (2006.01)
*A61N 5/06* (2006.01)

(52) U.S. Cl.
CPC ........... *A61K 41/0052* (2013.01); *A61K 33/26* (2013.01); *A61N 5/062* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| 8,202,268 B1 | 6/2012 | Wells et al. |
| 2011/0054236 A1 | 3/2011 | Yang et al. |

FOREIGN PATENT DOCUMENTS

| CN | 103055312 | 4/2013 |

OTHER PUBLICATIONS

Bumb et al., Synthesis and characterization of ultra-small superparamagnetic iron oxide nanoparticles thinly coated with silica. Nanotechnology, 19(33), 335601 (2008).
Cabral et al., Accumulation of sub-100 nm polymeric micelles in poorly permeable tumours depends on size. Nat Nanotechnol 6(12), 815-823 (2011).
Chen et al., Biocompatible Polysiloxane-Containing Diblock Copolymer PEO-b-P gamma MPS for Coating Magnetic Nanoparticles. Acs Appl Mater Inter 1(10), 2134-2140 (2009).
Chen et al., Gold Nanocages as Photothermal Transducers for Cancer Treatment. Small 6(7), 811-817 (2010).
Chen et al., Reducing non-specific binding and uptake of nanoparticles and improving cell targeting with an antifouling PEO-b-P gamma MPS copolymer coating. Biomaterials 31(20), 5397-5407 (2010).
Cheon et al., Shape evolution of single-crystalline iron oxide nanocrystals. J Am Chem Soc 126(7), 1950-1951 (2004).
Cherukuri et al., Targeted hyperthermia using metal nanoparticles. Adv Drug Deliver Rev 62(3), 339-345 (2010).
Chou et al., In Vitro and in Vivo Studies of FePt Nanoparticles for Dual Modal CT/MRI Molecular Imaging. J Am Chem Soc 132(38), 13270-13278 (2010).
Chu et al., Near-infrared laser light mediated cancer therapy by photothermal effect of Fe3O4 magnetic nanoparticles. Biomaterials 34(16), 4078-4088 (2013).
Dong et al., Facile Synthesis of Monodisperse Superparamagnetic Fe3O4 Core@hybrid@Au Shell Nanocomposite for Bimodal Imaging and Photothermal Therapy. Adv Mater 23(45), 5392-5397 (2011).
El-Sayed et al., Surface plasmon resonance scattering and absorption of anti-EGFR antibody conjugated gold nanoparticles in cancer diagnostics: applications in oral cancer. Nano Lett., 5(5), 829-834 (2005).
El-Sayed, Some interesting properties of metals confined in time and nanometer space of different shapes. Acc. Chem. Res., 34, 257-264 (2001).
Ficai et al., Synthesis of rod-like magnetite by using low magnetic field. Digets Journal of Nanomaterials and Biostructures, 6(3), 943-951 (2011).
Gu et al., Magnetic-field-assisted photothermal therapy of cancer cells using Fe-doped carbon nanoparticles. J Biomed Opt 17(1), 018003 (2012).
Habash et al., Thermal therapy, part 1: an introduction to thermal therapy. Crit Rev Biomed Eng 34(6), 459-489 (2006).
Hirsch et al., Nanoshell-mediated near-infrared thermal therapy of tumors under magnetic resonance guidance. P Natl Acad Sci USA 100(23), 13549-13554 (2003).
Ho et al., Shape-Controlled Growth and Shape-Dependent Cation Site Occupancy of Monodisperse Fe3O4 Nanoparticles. Chem Mater 23(7), 1753-1760 (2011).
Huang et al., A Reexamination of Active and Passive Tumor Targeting by Using Rod-Shaped Gold Nanocrystals and Covalently Conjugated Peptide Ligands. Acs Nano 4(10), 5887-5896 (2010).
Huang et al., Cancer cell imaging and photothermal therapy in the near-infrared region by using gold nanorods. J Am Chem Soc 128(6), 2115-2120 (2006).
Huang et al., Plasmonic photothermal therapy (PPTT) using gold nanoparticles. Lasers Med Sci., 23, 217-228 (2008).

(Continued)

*Primary Examiner* — Robert A Wax
*Assistant Examiner* — Randeep Singh
(74) *Attorney, Agent, or Firm* — Casimir Jones, S.C.; Jason Bond

(57) ABSTRACT

The present invention provides methods, systems, and devices for performing photothermal therapy (e.g., to treat cancer) using photothermal nanoparticles with a biocompatible coating surrounding a highly crystallized $Fe_3O_4$ core. In certain embodiments, the highly crystallized $Fe_3O_4$ core of the photothermal nanoparticles has an X-ray diffraction (XRD) pattern where the brightest diffraction ring is from the 440 plane. In some embodiments, the photothermal therapy is conducted with a device configured to emit electromagnetic radiation in the wavelengths between about 650 nm and 1000 nm, wherein the device further comprises a visible light source that allows a user to determine where the electromagnetic radiation is contacting a subject.

20 Claims, 23 Drawing Sheets

(56) References Cited

OTHER PUBLICATIONS

Hyeon et al., Synthesis of highly crystalline and monodisperse maghemite nanocrystallites without a size-selection process. J Am Chem Soc 123(51), 12798-12801 (2001).

Ji et al., Bifunctional gold nanoshells with a superparamagnetic iron oxide-silica core suitable for both MR imaging and photothermal therapy. J Phys Chem C 111(17), 6245-6251 (2007).

Kang et al., Synthesis and characterization of nanometer-size Fe3O4 and gamma-Fe2O3 particles. Chem Mater 8(9), 2209-2211 (1996).

Ke et al., Gold-Nanoshelled Microcapsules: A Theranostic Agent for Ultrasound Contrast Imaging and Photothermal Therapy. Angew Chem Int Edit 50(13), 3017-3021 (2011).

Kennedy et al., A New Era for Cancer Treatment: Gold-Nanoparticle-Mediated Thermal Therapies. Small 7(2), 169-183 (2011).

Kuo et al., Gold Nanorods in Photodynamic Therapy, as Hyperthermia Agents, and in Near-Infrared Optical Imaging. Angew Chem Int Edit 49(15), 2711-2715 (2010).

Lammers et al., Nanotheranostics and Image-Guided Drug Delivery: Current Concepts and Future Directions. Mol Pharmaceut 7(6), 1899-1912 (2010).

Lee et al., Antibiofouling polymer-coated superparamagnetic iron oxide nanoparticles as potential magnetic resonance contrast agents for in vivo cancer imaging. J Am Chem Soc 128(22), 7383-7389 (2006).

Lee et al., Designed synthesis of uniformly sized iron oxide nanoparticles for efficient magnetic resonance imaging contrast agents. Chem Soc Rev 41(7), 2575-2589 (2012).

Lee et al., Exchange-coupled magnetic nanoparticles for efficient heat induction. Nat Nanotechnol 6(7), 418-422 (2011).

Liao et al., Innovative ligand-assisted synthesis of NIR-activated iron oxide for cancer theranostics. Chem Commun 48(43), 5319-5321 (2012).

Link et al., How does a gold nanorod melt? J Phys Chem B 104(33), 7867-7870 (2000).

Link et al., J. Phys. Chem. B, 103, 8410-8426 (1999).

Liu et al., Optimization of surface chemistry on single-walled carbon nanotubes for in vivo photothermal ablation of tumors. Biomaterials 32(1), 144-151 (2011).

Loo et al., Immunotargeted nanoshells for integrated cancer imaging and therapy. Nano Lett., 5, 709-711 (2005).

Ma et al., Small Multifunctional Nanoclusters (Nanoroses) for Targeted Cellular Imaging and Therapy. Acs Nano 3(9), 2686-2696 (2009).

Melancon et al., Cancer Theranostics with Near-Infrared Light-Activatable Multimodal Nanoparticles. Accounts Chem Res 44(10), 947-956 (2011).

Melancon et al., Targeted multifunctional gold-based nanoshells for magnetic resonance-guided laser ablation of head and neck cancer. Biomaterials 32(30), 7600-7608 (2011).

Morris et al., Standard X-ray Diffraction Powder Patterns, NBS Monograph 25-Section 18, US Dept. of Commerce/National Bureau of Standards, Oct. 1981, 114 pages.

Patterson, The Scherrer formula for x-ray particle size determination. Phys Rev 56(10), 978-982 (1939).

Rockenberger et al., A new nonhydrolytic single-precursor approach to surfactant-capped nanocrystals of transition metal oxides. J Am Chem Soc 121(49), 11595-11596 (1999).

Shen et al., Monodisperse magnetites anchored onto carbon nanotubes: a platform for cell imaging, magnetic manipulation and enhanced photothermal treatment of tumors. J Mater Chem B 1(14), 1939-1946 (2013).

Sun et al., Monodisperse MFe2O4 (M=Fe, Co, Mn) nanoparticles. J Am Chem Soc 126(1), 273-279 (2004).

Tassa et al., Dextran-Coated Iron Oxide Nanoparticles: A Versatile Platform for Targeted Molecular Imaging, Molecular Diagnostics, and Therapy. Accounts Chem Res 44(10), 842-852 (2011).

Tian et al., Hydrophilic Flower-Like CuS Superstructures as an Efficient 980 nm Laser-Driven Photothermal Agent for Ablation of Cancer Cells. Adv Mater 23(31), 3542-3456 (2011).

Xie et al., Controlled PEGylation of monodisperse Fe3O4 nanoparticles for reduced non-specific uptake by macrophage cells. Adv Mater 19(20), 3163-3166 (2007).

Yang et al., Nano-graphene in biomedicine: theranostic applications. Chem Soc Rev 42(2), 530-547 (2013).

Yang et al., Multimodal Imaging Guided Photothermal Therapy using Functionalized Graphene Nanosheets Anchored with Magnetic Nanoparticles. Adv Mater 24(14), 1868-1872 (2012).

Yavuz et al., Gold nanocages covered by smart polymers for controlled release with near-infrared light. Nat Mater 8(12), 935-939 (2009).

Yguerabide et al., Light-scattering submicroscopic particles as highly fluorescent analogs and their use as tracer labels in clinical and biological applications. Anal. Biochem., 262, 137-156 (1998).

Yu et al., Synthesis of monodisperse iron oxide nanocrystals by thermal decomposition of iron carboxylate salts. Chem Commun (20), 2306-2307 (2004).

Zha et al., Uniform Polypyrrole Nanoparticles with High Photothermal Conversion Efficiency for Photothermal Ablation of Cancer Cells. Adv Mater 25(5), 777-782 (2013).

Zhang et al., Tailored Synthesis of Superparamagnetic Gold Nanoshells with Tunable Optical Properties. Adv Mater 22(17), 1905-1909 (2010).

Zhou et al., Luminescent gold nanoparticles with efficient renal clearance. Angew Chem Int Ed Engl 50(14), 3168-3172 (2011).

International Search Report and Written Opinion for PCT/US2014/050693, mailed Dec. 16, 2014, 9 pages.

Pre    48 h post injection

PHOTOTHERMAL THERAPY USING MAGNETIC NANOPARTICLES

CROSS-REFERENCE TO RELATED APPLICATIONS

The present invention claims priority benefit of U.S. Provisional Patent Application 61/865,840, filed Aug. 14, 2013, which is incorporated by reference in its entirety.

FIELD OF THE INVENTION

The present invention provides methods, systems, and devices for performing photothermal therapy (e.g., to treat cancer) using photothermal nanoparticles with a biocompatible coating surrounding a highly crystallized $Fe_3O_4$ core. In certain embodiments, the highly crystallized $Fe_3O_4$ core of the photothermal nanoparticles has an X-ray diffraction (XRD) pattern where the brightest diffraction ring is from the 440 plane. In some embodiments, the photothermal therapy is conducted with a device configured to emit electromagnetic radiation in the wavelengths between about 650 nm and 1000 nm, wherein the device further comprises a visible light source that allows a user to determine where the electromagnetic radiation is contacting a subject.

BACKGROUND

Photothermal therapy (PTT) employing near-infrared (NIR)-absorbing nanoparticles to generate heat from optical energy to kill cancer cells has gained great attention in recent years [1-4]. Most photothermal conducting agents are based on various gold (Au) nanostructures, including nanoshells [5, 6], nanorods [7, 8], and nanocages [9, 10]. In addition, the multifunctional probes with both therapeutic functions and imaging capabilities (e.g., magnetic resonance imaging) were also developed with traditional designs focusing on building Au nanoshell around magnetic nanoparticle core [11-15]. While various dual functional nanomaterials have been employed for PTT, virtually all those composed of iron oxide were nanocomposites also requiring a material that is thermally responsive to NIR light (usually gold) [11-15].

Despite the overwhelming potential of nanoparticle-mediated PTT to improve cancer treatment, lack of clinical approval restricts availability to a very narrow subset of cancer patients. The only nanoparticle-mediated PTT that has advanced to clinical trials is Aurolase therapy, consisting of Au nanoshells with a silica core, which was first investigated in patients with head and neck tumors and more recently for primary and metastatic lung tumors. However, the ~150 nm gold nanoshells are larger than the ideal size range to maximize exploitation of the enhanced permeability and retention (EPR) effect [5]. Although they are relatively biocompatible, they are not biodegradable and are too large to be excreted renally [16]; consequently, their long term effects are not well understood. Au nanorods, Au nanocages and Au nanoshells with iron oxide cores also face many of the same challenges as silica-core Au nanoshells [12]. Furthermore, nanorods lack photostability due to a "melting" phenomenon resulting from point and planar defects caused by application of laser light [17]. Clinical application of other non-biodegradable PTT mediators such as carbon nanotubes is also limited by potential long-term toxicity [18, 19].

Highly crystallized iron oxide nanoparticles (HCIONPs) made from thermal decomposition have been reported years ago by different groups with the ability to control the size from 5-40 nm [20-24, herein incorporated by reference in their entireties and specifically for describing HCIONPs]. These nanoparticles have been widely used as magnetic resonance imaging (MRI) contrast agents and imagine guidable drug carriers as well as inducers of magnetic hyperthermia under an alternating magnetic field [25-28]. Although magnetic iron oxide nanocrystals offer the ideal characteristics of clinically suitable nanoparticles and can meet all the criterion desired for PTT mediators, few works have been reported using magnetic nanoparticles only for effective PTT probably due to their low photothermal efficiency [29]. Last year researchers in Taiwan produced surface-modified IONPs (~440 nm) via a hydrothermal reaction that enhanced optical absorption in the NIR range, and it was postulated that this effect could be attributed to ligand-Fe complexes on the Fe3O4 nanoparticle surfaces [30].

SUMMARY OF THE INVENTION

The present invention provides methods, systems, and devices for performing photothermal therapy (e.g., to treat cancer) using photothermal nanoparticles with a biocompatible coating surrounding a highly crystallized $Fe_3O_4$ core. In certain embodiments, the highly crystallized $Fe_3O_4$ core of the photothermal nanoparticles has an X-ray diffraction (XRD) pattern where the brightest diffraction ring is from the 440 plane. In some embodiments, the photothermal therapy is conducted with a device configured to emit electromagnetic radiation in the wavelengths between about 650 nm and 1000 nm, wherein the device further comprises a visible light source that allows a user to determine where the electromagnetic radiation is contacting a subject.

In some embodiments, the present invention provides methods of treating at least one tumor in a subject comprising: a) treating a subject with a composition comprising photothermal nanoparticles, wherein the subject comprises at least one tumor, wherein the photothermal nanoparticles individually comprise a biocompatible coating surrounding a highly crystallized $Fe_3O_4$ core, and wherein the treating is under conditions such that at least a portion of the photothermal nanoparticles infiltrate the at least one tumor; and b) subjecting the subject to photothermal therapy on the first day of a three week period, wherein the photothermal therapy comprises the use of a device that emits electromagnetic radiation and causes the at least one tumor to be reduced in size or become undetectable at the end of the three week period.

In some embodiments, the present invention provides methods of treating at least one tumor in a subject comprising: a) treating a subject with a composition comprising photothermal nanoparticles, wherein the subject comprises at least one tumor, wherein the photothermal nanoparticles individually comprise a biocompatible coating surrounding a highly crystallized $Fe_3O_4$ core, and wherein the treating is under conditions such that at least a portion of the photothermal nanoparticles infiltrate the at least one tumor; and b) subjecting the subject to photothermal therapy: i) on the first day of a three week period, and ii) on no more than four or three additional days of the three week period, wherein the photothermal therapy comprises the use of a device that emits electromagnetic radiation and causes the at least one tumor to be reduced in size or become undetectable at the end of the three week period.

In certain embodiments, the present invention provides methods of treating at least one tumor in a subject comprising: subjecting a subject to photothermal therapy: i) on the first day of a three week period, and optionally ii) on no more than four three additional days of the three week period, wherein the subject has previously been treated with a composition comprising photothermal nanoparticles, wherein the subject comprises at least one tumor, wherein the photothermal nanoparticles individually comprise a biocompatible coating surrounding a highly crystallized $Fe_3O_4$ core; and wherein the photothermal therapy comprises the use of a device that emits electromagnetic radiation and causes the at least one tumor to be reduced in size or become undetectable at the end of the three week period.

In particular embodiments, the present invention provides methods of treating cancer in a subject comprising: a) treating a subject with a composition comprising photothermal nanoparticles, wherein the subject comprises at plurality of cancer cells, wherein the photothermal nanoparticles individually comprise a biocompatible coating surrounding a highly crystallized $Fe_3O_4$ core, wherein the highly crystallized $Fe_3O_4$ core of the photothermal nanoparticles has an X-ray diffraction (XRD) pattern where the brightest diffraction ring is from the 440 plane, and wherein the treating generates a plurality of photothermal nanoparticle-impregnated cancer cells in the subject; and b) subjecting the subject to photothermal therapy using a device that emits electromagnetic radiation such that at least a portion of the photothermal nanoparticle-impregnated cancer cells are damaged or killed.

In some embodiments, the present invention provides methods of treating cancer in a subject comprising: a) providing a subject who comprises a plurality of cancer cells impregnated with photothermal nanoparticles, wherein the photothermal nanoparticles individually comprise a biocompatible coating surrounding a highly crystallized $Fe_3O_4$ core, wherein the highly crystallized $Fe_3O_4$ core of the photothermal nanoparticles has an X-ray diffraction (XRD) pattern where the brightest diffraction ring is from the 440 plane; and b) subjecting the subject to photothermal therapy using a device that emits electromagnetic radiation such that at least a portion of the cancer cells are damaged or killed.

In certain embodiments, the present invention provides systems comprising: a) a composition comprising photothermal nanoparticles, wherein the photothermal nanoparticles individually comprise a biocompatible coating surrounding a highly crystallized $Fe_3O_4$ core, and wherein the highly crystallized $Fe_3O_4$ core has an X-ray diffraction (XRD) pattern where the brightest diffraction ring is from the 440 plane; and b) a device configured to emit electromagnetic radiation at least in the wavelengths between about 650 nm and 1000 nm.

In particular embodiments, the present invention provides systems comprising: a) a composition comprising photothermal nanoparticles, wherein the photothermal nanoparticles individually comprise a biocompatible coating surrounding a highly crystallized $Fe_3O4$ core; and b) a device configured to emit electromagnetic radiation at least in the wavelengths between about 650 nm and 1000 nm, wherein the device further comprises a visible light source, wherein the visible light source allows a user to determine where the electromagnetic radiation is contacting a subject.

In particular embodiments, the present invention provides devices or systems comprising: a) a near infrared (NIR) laser or other NIR emitting device, and b) a visible light source that emits visible light, wherein the visible light source is positioned with respect to the NIR laser such that the visible light indicates where the NIR laser is shining on a subject.

In certain embodiments, the highly crystallized $Fe_3O_4$ core of the photothermal nanoparticles has an X-ray diffraction (XRD) pattern where the brightest diffraction ring is from the 440 plane. In other embodiments, the highly crystallized $Fe_3O_4$ core of the photothermal nanoparticles has a preferred lattice orientation along the 400 and 440 XRD diffraction planes.

In particular embodiments, the subject is subjected to the photothermal therapy on no more than two additional days of the three week period. In certain embodiments, the subject is subjected to the photothermal therapy one no more than one additional day of the three week period. In some embodiments, the subject is subjected to the photothermal therapy on only the first day of the three week period.

In other embodiments, the photothermal therapy causes the at least one tumor to be reduced in size at least 50% (e.g., at least 50% . . . 65% . . . 79% . . . 86% . . . 93% . . . or 99%) at the end of the three week period. In some embodiments, the treating comprises administering the photothermal nanoparticles to the subject intravenously or intratumorally. In further embodiments, the photothermal nanoparticles have a size between 18 nm and 30 nm (e.g., 18 nm . . . 23 nm . . . 26 nm . . . and 30 nm).

In certain embodiments, the device emits electromagnetic radiation with a wavelength between about 865 nm and 1000 nm. In other embodiments, the device emits electromagnetic radiation with a wavelength between about 650 nm and 1000 nm. In further embodiments, the device comprises a laser and/or LED. In additional embodiments, the length of treatment on the first day, and on any of the three additional days is between 5 and 15 minutes (e.g., 5 . . . 9 . . . 12 . . . and 15 minutes).

In some embodiments, the device further comprises a visible light source, wherein the visible light source allows a user to determine where the electromagnetic radiation is contacting the subject. In certain embodiments, the device further comprises a component that reveals the temperature of the subject's skin. In some embodiments, the device further comprises a thermal imaging device.

In particular embodiments, the subject is a human, cat, dog, or livestock animal. In particular embodiments, the photothermal nanoparticles are present in the composition at a concentration of between 1.0 and 10.0 mg Fe/mL (e.g. 1.0 . . . 3.0 . . . 6.0 . . . and 10.0 mg Fe/mL). In some embodiments, the subject is treated with a dosage of the photothermal nanoparticles of 10-40 mg Fe/Kg of the subject's body weight (e.g., 10 . . . 19 . . . 26 . . . 34 . . . and 40 mg Fe/Kg of subject's body weight). In other embodiments, the at least one tumor is selected from the group consisting of: a breast tumor, a skin tumor, a kidney tumor, a lymph node tumor, a brain tumor, a liver tumor, a pancreatic tumor, a colon tumor, a lung tumor, an esophagus tumor, and prostate tumor. In certain embodiments, the biocompatible coating comprises a material selected from the group consisting of: polyethylene glycol, triblock copolymer, PEO-b-PPO-b-PEO (F121), PEO-b-PVP, glucosylated poly(pentafluorostyrene), chitosan, silica, and gum Arabic, gluconic acid, lactobionic acid, polyacrylic acid, apatite, and Casein.

DETAILED DESCRIPTION

Figure 1:
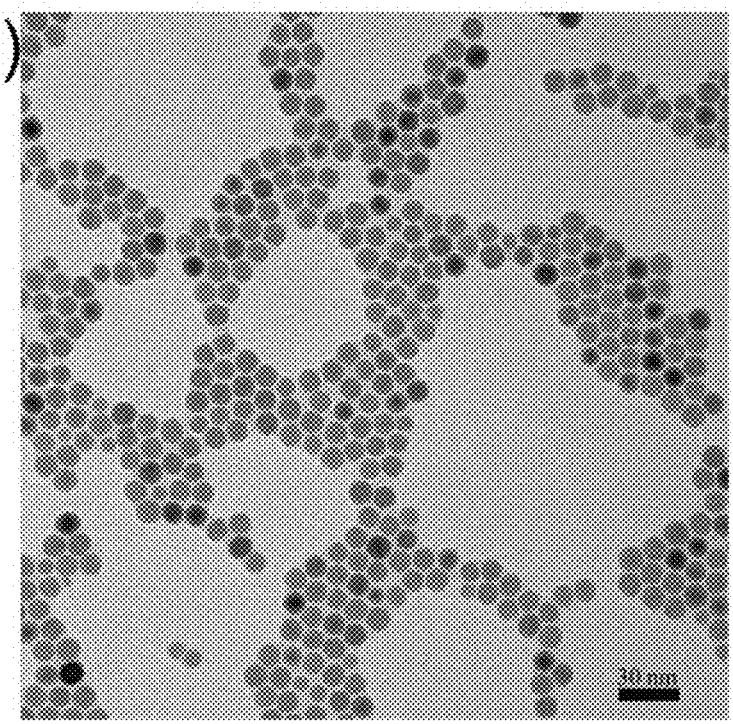
FIGS. 1a-d. (a) TEM image of the as-prepared (in Example 1) magnetic nanocrystals. (b) High-resolution TEM image of mangnetic nanocrystals. (c) TEM image (negative stained) of polymer coated mangetic nanocrystals. (d) Measured temperature of increasing concentrations of magnetic nanocrystals in water. All temperatures were measured during 10 minutes of illumination with a diode laser (λ=885 nm) at a fluence rate of 2.5 W/cm2.
Figure 1:
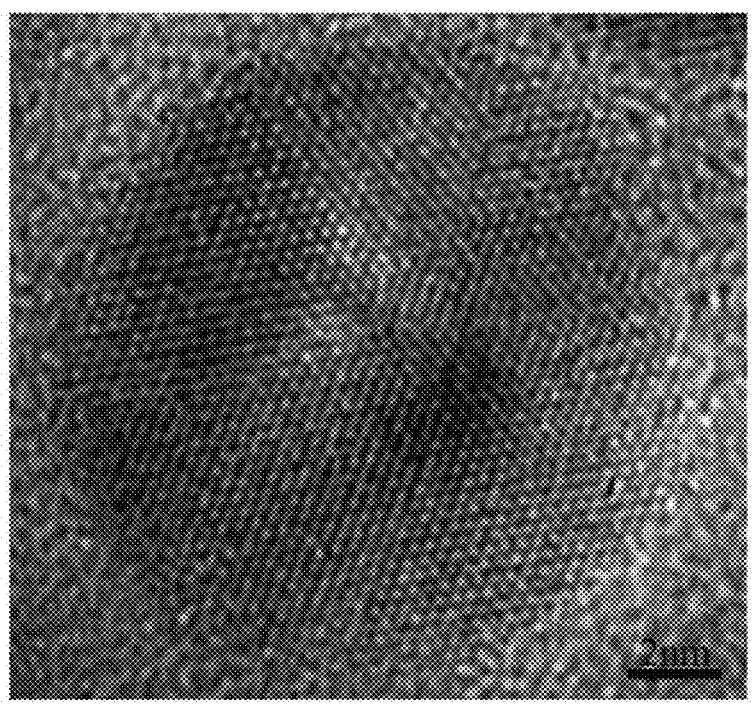
Figure 1:
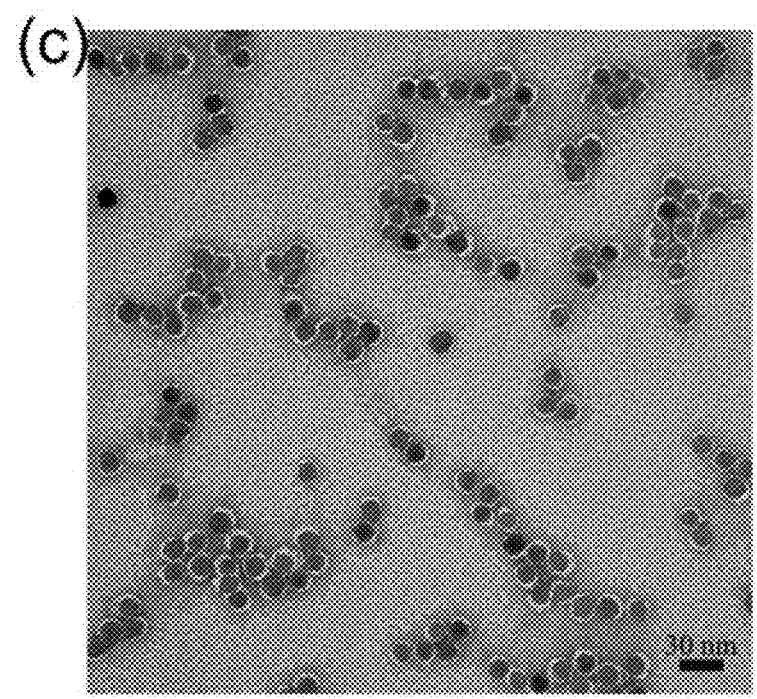
Figure 1:
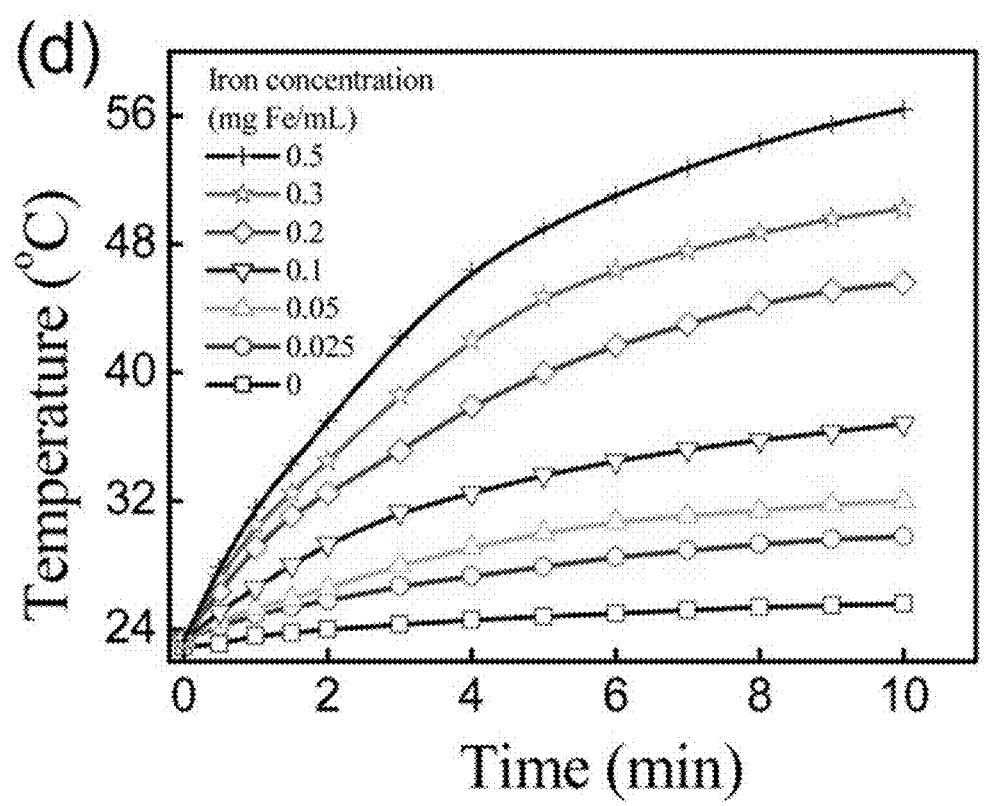

The present invention provides methods, systems, and devices for performing photothermal therapy (e.g., to treat cancer) using photothermal nanoparticles with a biocompatible coating surrounding a highly crystallized $Fe_3O_4$ core. In certain embodiments, the highly crystallized $Fe_3O_4$ core of the photothermal nanoparticles has an X-ray diffraction (XRD) pattern where the brightest diffraction ring is from the 440 plane. In some embodiments, the photothermal therapy is conducted with a device configured to emit electromagnetic radiation in the wavelengths between about 650 nm and 1000 nm, wherein the device further comprises a visible light source that allows a user to determine where the electromagnetic radiation is contacting a subject.

In certain embodiments, the photothermal nanoparticles described herein are used for treating a conditions such as cancer and/or a condition associated with vascular tissue or cells, for example, atherosclerosis. In general, the photothermal nanoparticles described herein are targeted to cells, tissue or other site of interest associated with the condition, will absorb near infrared radiation delivered thereto and, upon becoming heated by the NIR, result in selective thermolysis or ablation or other damage or cell death without damaging untargeted cells or tissues. Devices and methods for delivering radiation of a particular wavelength, such as by, but not limited to, lasers, to a targeted site are well-known and standard in the art. In some embodiments, the photothermal nanoparticles are used as MR contrast agents, with or without subsequent photothermal therapy.

EXAMPLES

Example 1

Highly Crystallized Iron Oxide Nanoparticles for Photothermal Therapy

This Examples describes the generation and characterization of highly crystallized iron oxide nanoparticles, and a description of their use in vivo for photothermal therapy to treat cancer.

Materials and Methods

Materials

Iron oxide (III) (FeO(OH), hydrated, catalyst grade, 30-50 mesh), oleic acid (technical grade, 90%), 1-octadecene (technical grade, 90%), anhydrous tetrahydrofuran (THF, 99.8%), ammonium iron (II) sulfate hexahydrate (Fe(NH4)2(SO4)2.6H2O, ACS reagent, 99%), o-phenanthroline monohydrate (ACS reagent, 99%), hydroquinone (ACS reagent, 99%), nitric acid (ACS reagent, 70%), and hydrochloric acid (ACS reagent, 37%) were purchased from Aldrich. Commercial magnetic nanoparticles (FeREX) were obtained from BioPAL.

Synthesis of HCIONPs

HCIONPs (15 nm in diameter) were synthesized in organic solvent by thermal decomposition as reported previously with a slight modification [24]. Briefly, a mixture of 0.890 g FeO(OH), 19.8 g oleic acid and 25.0 g 1-octadecene in a three-neck flask was heated under stirring to 200° C. under N2, 30 minutes later the temperature was set at 220° C. for 1 h, then the temperature was increased gradually to 310° C. (20° C./5 minutes) and kept at this temperature for 1 h. The solution became black when the temperature was increased to 320° C. and kept at this temperature for 1 h. After the reaction was completed, the reaction mixture was cooled and the nanocrystals were precipitated by adding chloroform and acetone.

Coating of HCIONPs with Polysiloxane-Containing Diblock Copolymer

Diblock copolymer (PEO-b-PγMPS) was synthesized by the reversible addition of fragmentation chain transfer (RAFT) polymerization as previously reported [32]. The method for coating single core nanocrystals was reported previously with a slight modification [32]. Briefly, the purified nanocrystals (100.0 mg) were dispersed in 10 mL of anhydrous THF and then mixed with the newly synthesized copolymer (1.00 g) in 10 mL of anhydrous THF. After being aged for four days, the mixture was added dropwise into 100 mL of water with gentle magnetic stirring. THF in the solution was removed by dialysis using deionized water. The resultant solution was then purified by using a magnetic separator (Frantz laboratory). This wash-resuspend step was repeated three times. The average hydrodynamic diameter was measured using a dynamic light scattering instrument (Malvern Zeta Sizer Nano S-90). The magnetic nanocrystals were viewed by transmission electron microscopy (TEM) (Philips CM-100 60 kV), with the polymer coating made visible by negative staining with OsO4. High-resolution TEM was taken on a JEOL 3011 microscope. UV-vis-NIR spectra were recorded in a BioTek micro-plate reader (Synergy 2) using 200 μL of aqueous solution.

Determination of Iron Concentration Using Spectrophotometry

10 μL of concentrated HCIONP solutions was diluted with 2 mL of Milli-Q water, followed by adding 200 μL of concentrated HCl solution. After two days, sodium citrate was added to adjust the solution pH to 3.5. Then 2 mL of hydroquinone (10 g/L) and 3 mL of o-phenanthroline (2.5 g in 100 mL of ethanol and 900 mL of water) were added to the solution followed by adjusting to a specific volume using Milli-Q water. Five standard Fe solutions using Fe(NH4)2(SO4)2.6H2O were also made. To determine the solution concentration of iron, calibration curves were generated by measuring optical absorbance of solutions at 508 nm.

Photothermal Effect of HCIONPs in Aqueous Solution

To study the photothermal effect of HCIONPs induced by NIR light, the aqueous solutions (1.0 mL) of the nanocrystals with different Fe concentrations in a cuvette were irradiated using an NIR laser (885 nm, 2.5 W/cm2, spot size, 5×8 mm2, MDL-III-885, OPTO Engine LLC, Midvale, Utah) for 10 minutes. The temperature of the solutions was measured by a digital thermometer.

Synchrotron-XRD for Aqueous Dispersed Magnetic Nanoparticles

X-ray diffraction experiments were conducted in a transmission mode at x17c station of National Synchrotron Light Source, Brookhaven National Laboratory. The x-ray is monochromated to a wavelength of 0.4066 Å and the beam size is 20×30 μm2. The diffraction image was recorded with a CCD detector and then integrated to normal diffraction profiles by using program Fit2D. The instrument parameters were calibrated with CeO2 as an external standard.

Cell Culture

SUM-159 cells were cultured under a 5% CO2 environment in F12 media (Invitrogen, Carlsbad, Calif.) supplemented with 5% fetal bovine serum (Fisher Scientific, Pittsburgh, Pa.), 1% antibiotic-antimycotic (Invitrogen, Carlsbad, Calif.), 5 μg/mL insulin (Sigma-Aldrich, St Louis, Mo.), 1 μg/mL hydrocortisone (Sigma-Aldrich, St Louis, Mo.), and 4 μg/mL gentamicin (Invitrogen, Carlsbad, Calif.).

Xenograft Mouse Model

All studies involving mice were conducted in accordance with a standard animal protocol approved by the University Committee on the Use and Care of Animals at the University of Michigan. Five week old nude mice were obtained from Charles River Breeding Laboratories. Xenograft formation was generated by direct injection of 5×10$^5$ SUM-159 cells, suspended in matrigel, into the exposed no. 4 inguinal mammary pad. Tumor detection was assessed by palpation and once identified measurement of tumor volume was carried out using digital calipers and calculated by volume=(width)2×length/2.

Biodistribution

SUM-159 tumor-bearing BALB/c mice were used for this study. Mice in one group (four mice in each group) were intravenously injected with HCIONPs (as-prepared polymer-coated HCIONPs were the only type used for all in vivo studies in this example) at dose of 15 mg Fe/Kg mouse body weight. Mice in another group were used as a control without any injection. After 48 h, animals were sacrificed. Blood samples were collected by terminal heart puncture and centrifuged for 10 minutes at 5,000 rpm to separate the serum. The tissue samples of tumor, liver, spleen, lungs, kidney, heart, brain, stomach, and muscle were collected and weighed. To determine the iron concentrations in the serum or major organs, 200 μL of serum or whole organ tissue samples were digested in 1 mL of nitric acid (2 mL for liver). After filtration (acrodisc syringe filters, PTFE membrane, diameter 13 mm, pore size 0.45 μm), the volumes of solutions were adjusted to 10.0 mL and the iron concentration was analyzed using inductively coupled plasma optical emission spectrometry (ICP-OES) with Yttrium as the internal standard.

In Vitro MRI and T2 Relaxivity Measurement

Magnetic resonance imaging (MRI) studies were carried out by using a MRI scanner at 7.4-T field strength. For T2 measurements, a multiecho fast spin-echo sequence was used to simultaneously collect a series of data points at different echo times (TE=15-90 ms with an increment of 15 ms). The T2 relaxation time of each nanoparticle sample was calculated by fitting the decay curve on a pixel-by-pixel basis by using a nonlinear monoexponential algorithm $M(TE)=M0 \exp(-TEi/T2)$, where TE is the echo time, M(TE) is the MRI signal intensity at which TE is used.

MRI of Tumor-Bearing Mice Administered with as-Prepared IONPs

Tumor-bearing nude mice were scanned with a wrist coil to collect pre- and post-contrast enhanced MRI data. Images from pre- and post-contrast administration were compared to evaluate the contrast enhancement. Mice were imaged before and 48 h after tail vein injection with as-prepared magnetic nanoparticles (20 mg Fe/Kg mouse body weight). T2 weighted fast spin echo sequence was used to obtain T2 relaxometry of the tumor tissue. The averaged signal intensity of whole tumors was calculated manually using ImageJ (U.S. National Institutes of Health, Bethesda, Md., USA) for comparing the signal intensity before and after injection of magnetic nanoparticles.

In Vivo PTT

Tumor-bearing nude mice were randomly allocated into four groups (five mice in each group) when the solid SUM-159 tumors had grown to ~40 mm3. Mice in group 1 were intravenously injected with magnetic nanoparticles (20 mg Fe/Kg mouse body weight). 48 h post injection, tumors were irradiated with a diode laser ($\lambda$=885 nm) at a fluence rate of 2.5 W/cm2 for 10 minutes. The highest tumor surface temperature was recorded by an infrared camera (MR Systems, i7, Boston, Mass.) before and after application of the laser. Mice in group 2 were only injected with magnetic nanoparticles without laser treatment. Mice in group 3 were injected with PBS plus laser treatment. Untreated mice were in group 4.

Long Term Toxicity of Administered Magnetic Nanoparticles

Tumor-survived mice after photothermal therapy were sacrificed four months after magnetic nanoparticles injection and the main organs were collected and analyzed by ICP-OES. Healthy mice without magnetic nanoparticles injection were used as control (three mice in each group).

Histology

Mice were humanely euthanized by CO2 inhalation two days following a single I.V. bolus dose of nanoparticles. The harvested tissue was formalin-fixed, embedded in paraffin and sectioned. Unstained slides were dewaxed using xylene and rehydrated using graded alcohol. Rehydrated slides were stained with Hematoxylin and eosin (H&E staining) for visualization of nucleic acids and cytoplasm.

Statistical Analysis

Differences in biodistribution data were analyzed using a two-tailed unpaired Student's t-test, with p<0.05 considered statistically significant.

Results

In Vitro PTT Using HCIONPs

Figure 8:
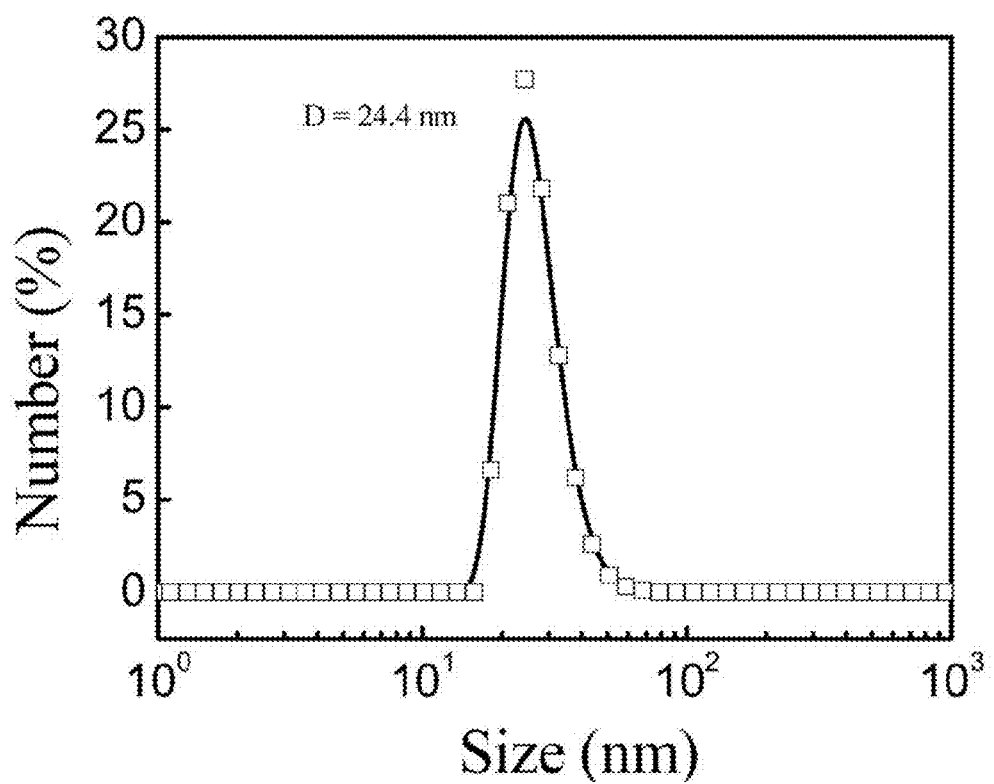
FIG. 8. Hydrodynamic size distribution of polymer coated as-prepared HCIONPs in water.
Figure 9:
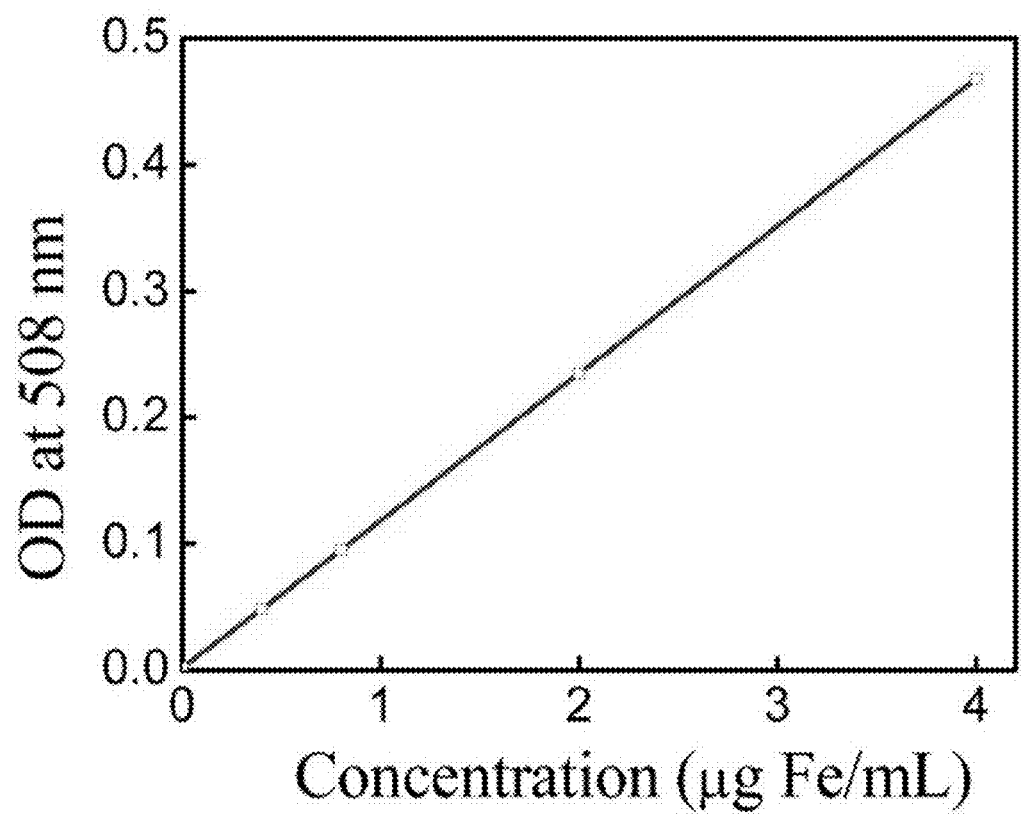
FIG. 9. The calibration curve for determination of iron colorimetrically using 1,10-phenanthroline.

Thermal decomposition of an iron precursor can generate high crystallized iron oxide nanoparticles (IONPs) [23, 24]. This is in stark contrast to the simple co-precipitation of ferrous (Fe2+) and ferric (Fe3+) ions by a base in an aqueous solution [33, 34]. TEM micrographs of the as-described nanoparticles demonstrate the high quality of the HCIONPs as shown in FIG. 1a. The particles have a narrow size distribution (5-10%) with an average diameter of 15 nm. The spontaneously formed, separate but ordered assembly pattern is an additional confirmation of the monodispersity of the nanocrystals. The high-resolution transmission electron microscopy (HRTEM) shown in FIG. 1b illustrates the highly crystalline nature of the as-prepared nanoparticles. These high quality nanocrystals are hydrophobic and prone to aggregation in physiological conditions [32, 35]. Therefore, they are not readily applicable for biomedical applications without proper surface modifications to render them soluble in aqueous solution. To this end, a biocompatible coating (in this case a polysiloxane-containing amphiphilic copolymer) is utilized as coating material, which individually dispersed magnetic nanocrystals for in vivo applications [36]. The negative stained TEM image of polymer-coated HCIONPs as shown in FIG. 1c clearly reveals the core-shell structure with a thin polymer layer around 3-5 nm thick with all the nanocrystals individually dispersed. Measuring their hydrodynamic size using dynamic light scattering (DLS) confirms an average size of 24.4 nm (FIG. 8). The resultant polymer-coated HCIONPs are stable in various physiological conditions including phosphate buffer and cell culture media [36]. These highly stable nanoparticles with small overall size are favorable for tumor accumulation and tissue penetration through EPR effect [37]. Before evaluating the PTT of as-prepared HCIONPs in vivo studies, their photothermal effect in aqueous solution was evaluated. In order to investigate the temperature elevation induced by NIR laser irradiation of these HCIONPs, a continuous-wave diode laser was used with a center wavelength of 885 nm. FIG. 1d shows the temperature profiles for 10 minutes of laser irradiation of nanoparticle solutions with iron concentration ranging from zero to 0.5 mg Fe/mL (iron concentration was determined colorimetrically using 1,10-phenanthroline, FIG. 9). At a nanoparticle concentration of 0.5 mg Fe/mL, the nanocrystal solution (1.0 mL in a cuvette) shows a significant temperature rise from room temperature to 56.4° C. Furthermore, dose-dependent increases in temperature were observed for iron concentrations of 0.025 to 0.5 mg Fe/mL. This photothermal effect induced by NIR light irradiation tends to match the recent study using polypyrrole nanoparticles, a newly found high efficiency photothermal conversion agent [38]. It was reported that a solution of 30 μg/mL polypyrrole nanoparticles could cause a temperature increase from 21.3 to 55.8° C. after NIR illumination for 10 minutes.

Biodistribution of HCIONPs in Tumor-Bearing Mice

Figure 2:
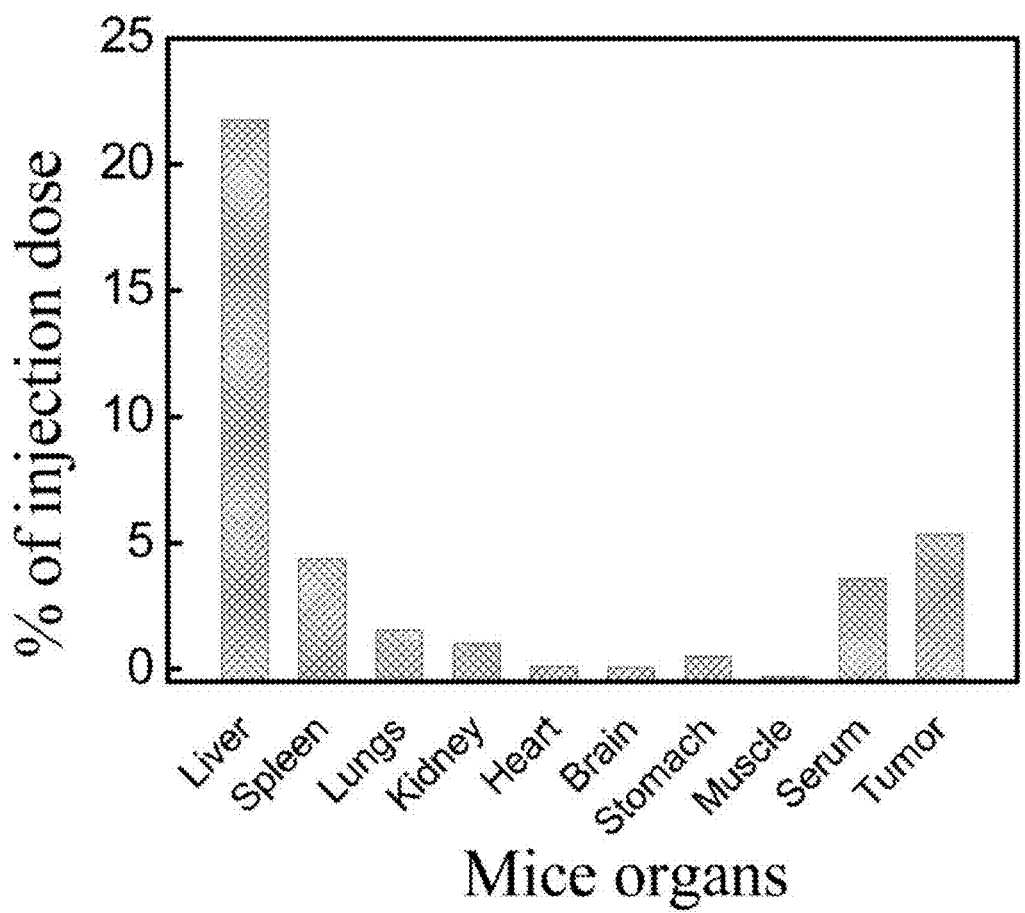
FIG. 2. Percentage of injection dose (ID) in main organs at 48 h post intravenous injection of magnetic nanoparticles. The value shown here has been subtracted with averaged background from control mice.
Figure 10:
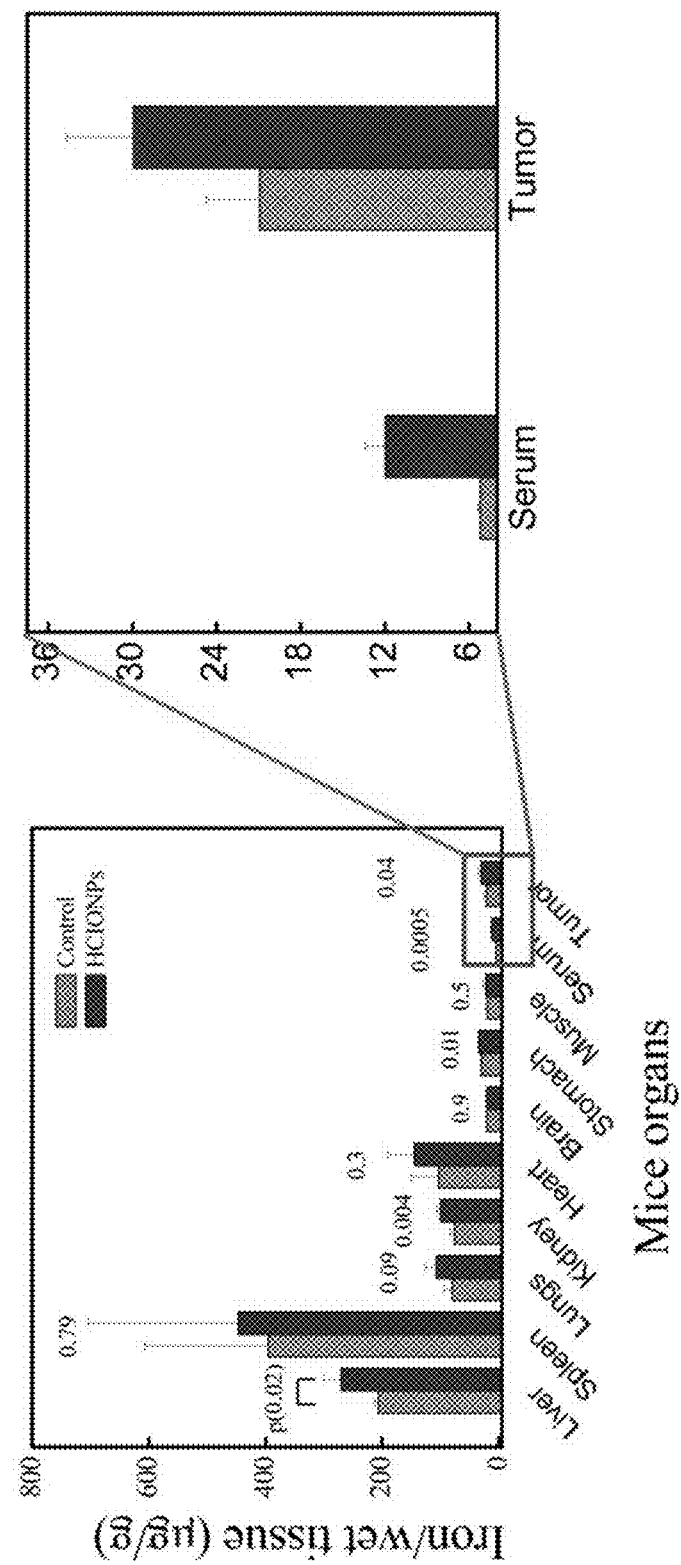
FIG. 10. Biodistribution of polysiloxane-containing polymer coated HCIONPs in the major organs. The data is recorded from whole organ taken at 48 h post tail vein injection and the iron concentration is determined by ICP-OES. Each group has four mice, and the error bar is standard deviation. Numbers are p-value of iron content in each organ between two group mice.

These highly crystalline, small, photo-stable nanocrystals are ideally suited for in vivo PTT. However, to effectively eliminate malignancies nanoparticles must first accumulate within the tumor site. Two common methods employed for targeting tumors rely passively on the EPR effect or activity [39]. Application of an external magnetic field can assist PTT of cancer cells by actively capturing magnetic nanoparticles in targeted areas, which was most recently reported using Fe-doped carbon nanoparticles [40]. In this example, the small overall size and antibiofouling polymer coating are particularly well suited for effective accumulation of nanocrystals to tumor tissue via the EPR effect. To test our hypothesis, the biodistribution of polysiloxane-containing polymer-coated HCIONPs was evaluated in tumor-bearing mice. 48 h post injection, major organs and serum were collected, weighed, and digested with nitric acid and then analyzed by inductively coupled plasma optical emission spectrometry (ICP-OES) (FIG. 10). The data shows that the iron concentration in the liver is increased by 30% compared to control mice, but no significant difference was found between spleens, revealing that these administered HCIONPs were not trapped in spleen. It is worth noting that iron/wet tissue in kidney also increased by 30% with p value at 0.004, indicating that magnetic nanoparticles may ultimately be eliminated by urinary excretion. As expected, the iron concentration in tumor tissue increased by 43% comparing to the control group. The data is further analyzed as percentage of injection dose (ID) after subtraction of the background iron level, as shown in FIG. 2. After 48 h, 22% of the ID is detected in liver and 4.3% in spleen. Interestingly, 5.3% of the ID accumulates within the tumor, which is considerably higher than recent reports using targeted nanoparticles [39]. These results suggest that the antibiofouling properties of polysiloxane-containing copolymer-coated nanocrystals result in enhanced evasion of the immune system leading to effective tumor accumulation.

MRI Imaging of Tumors Using HCIONPs

Figure 3:
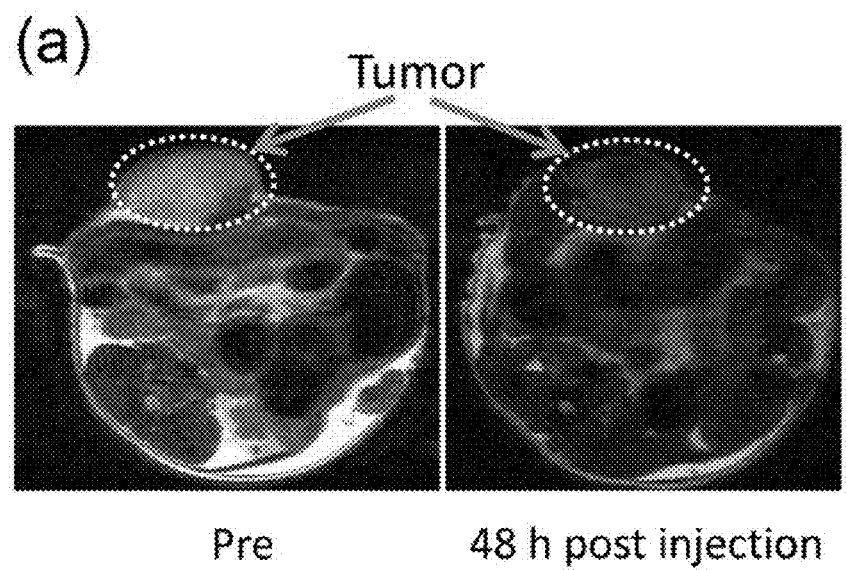
FIG. 3. (a) MR images of SUM-159 tumor-bearing mouse of pre (left) and 48 h post tail-vein injection (right) of polymer coated as-prepared magnetic nanocrystals at a dosage of 20 mg Fe/Kg body weight. (b) Surface temperature changes of tumors in mice (48 h post intravenously injected with magnetic nanocrystals or PBS as control) after laser irradiation for 10 minutes.
Figure 3:
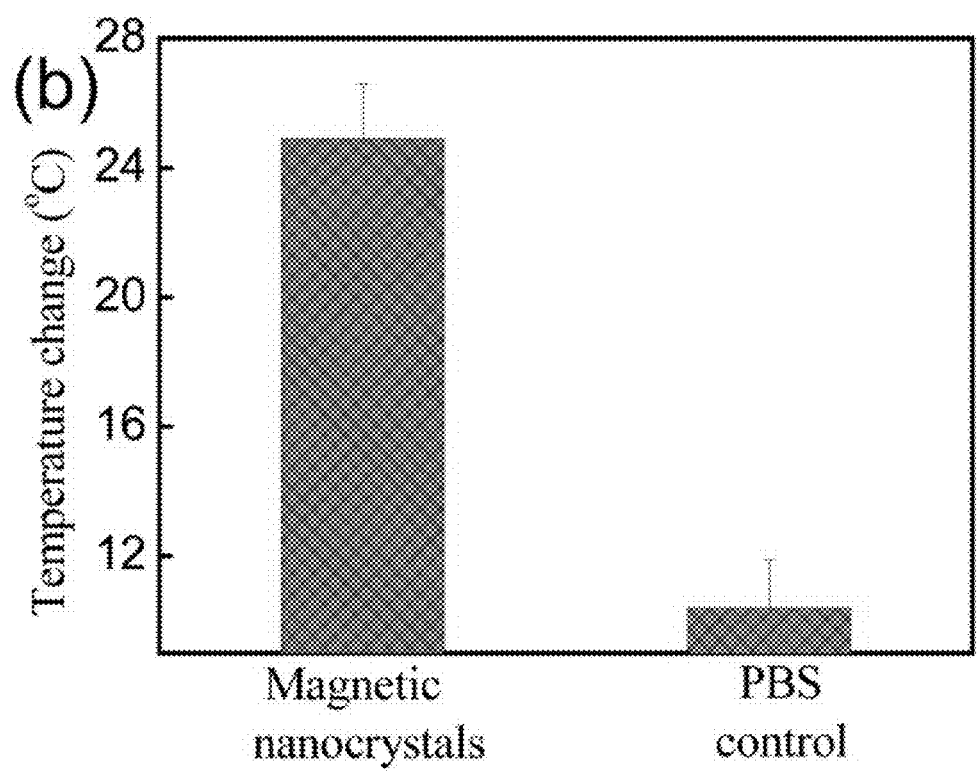
Figure 11:
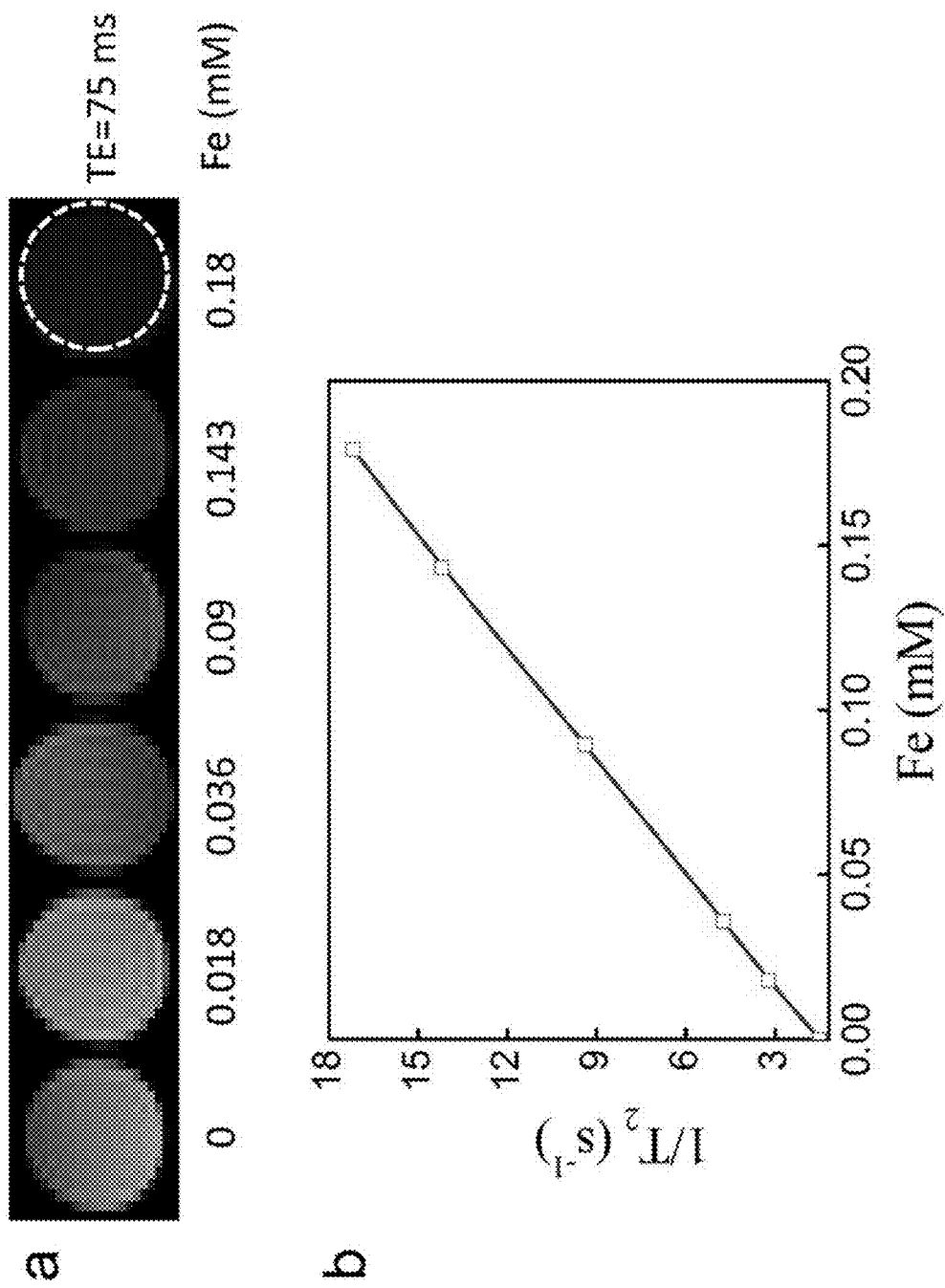
FIG. 11. (a) T2-weighted MR images (b) T2 relaxation rates (R2) of as-prepared HCIONP solutions at each concentration.

To assess the multimodality properties of as-prepared HCIONPs, they were also tested as MRI imaging contrast agents. T2-weighted MR images of nanocrystals at increasing concentrations from zero to 0.18 mM reveal the concentration-dependent darkening effect (FIG. 11a) with the transverse relaxivity (r2) measured at 87.4 mM–1S–1 (FIG. 11b), consistent with the previous reports [13]. This was then followed by in vivo evaluation of the T2 weighted MR imaging capability. MR imaging of SUM-159 tumor-bearing mice was conducted after intravenous injection of magnetic nanocrystals, revealing an obvious darkening effect with a T2-MR signals decreases by ~40% in the tumor 48 h post injection as shown in FIG. 3a. This suggests that as-prepared HCIONPs could be used to both induce and monitor the photothermal therapeutic effect.

In Vivo PTT Using HCIONPs

In vivo PTT was studied using as-prepared HCIONPs administered to human xenograft bearing immunocompromised mice. Nude mice bearing SUM-159 tumors were intravenously injected with as-prepared polymer-coated HCIONPs (a dose of 20 mg Fe/Kg mouse body weight) or PBS as control [13]. 48 h post injection, tumors were irradiated with the same laser conditions as in the above in vitro solution study. An infrared camera (FLIR i7, Boston, Mass.) was used to monitor the surface temperature of mice and tumors. The result of enhanced photothermal effect from HCIONPs is shown in FIG. 3b. The surface temperature of the tumor site in mice treated with HCIONPs increases from approximately 35° C. to ~60° C. after laser irradiation for 10 minutes, with an average tumor temperature increase of 25±1.7° C. (five mice per treatment group). During tumor irradiation, areas of mice which were not exposed to the NIR laser show a negligible temperature increase. In contrast, the surface temperatures of tumors on control treated mice shows only an increase to ~47° C. with an average tumor temperature increase of 10.5±1.5° C. after laser irradiation with the same laser power and duration of exposure. The average temperature increase for mice injected with nanoparticles is ~15° C. higher than that in control group after laser irradiation. Previous reports indicate that 1 h maintenance at 42° C. is necessary to kill cells, with effective exposure time shortening to 3-4 minutes when temperature is increased to 70-80° C. [41]. Dong et al. also reported that a tumor tissue temperature increase to 60° C. is high enough to kill cancer cells after five minutes of laser irradiation for mice intratumorally injected with Fe3O4/Au core/shell nanocomposites [12].

Figure 4A:
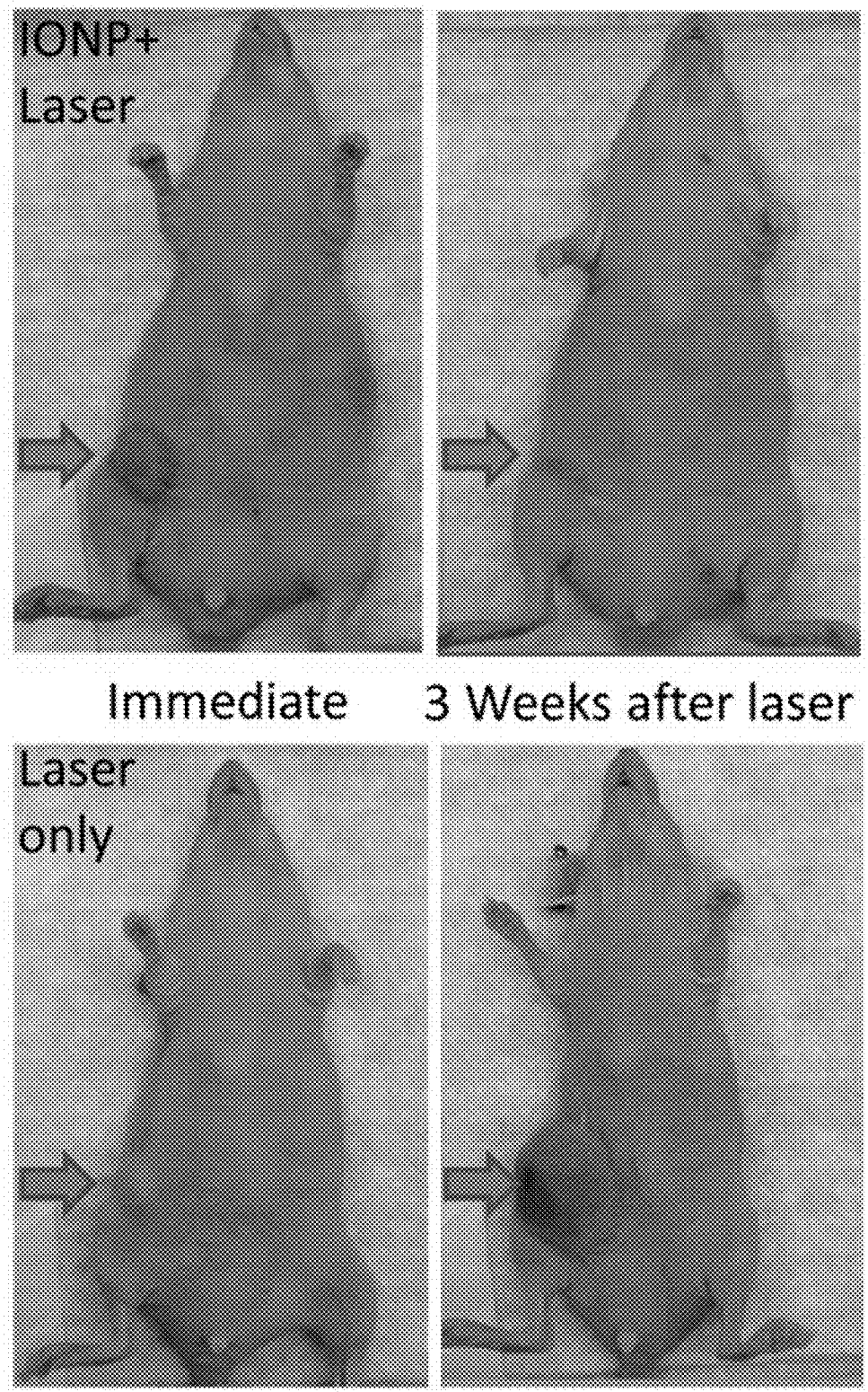
FIGS. 4a-d. (a) Representative photos of SUM-159 tumor-bearing mice of both immediate and 3 weeks after laser treatment. Laser wavelength=885 nm. Power density=2.5 W/cm2. Irradiation time=10 minutes. Arrows point the tumor sites. H & E staining of tumor tissues from mouse treated with nanoparticles plus laser irradiation (b) and control mouse without any treatment (c). (d) Anti-tumor efficacy of four different groups of mice before and 3 weeks post various treatments. Four groups (5 mice for each group) are magnetic nanocrystals injected mice with laser irradiation (G1), nanocrystals injected mice without laser irradiation (G2), laser treated mice without injection of nanoparticles (G3), and control mice injected with PBS (G4). Error bars are based on standard deviations.
Figure 4:
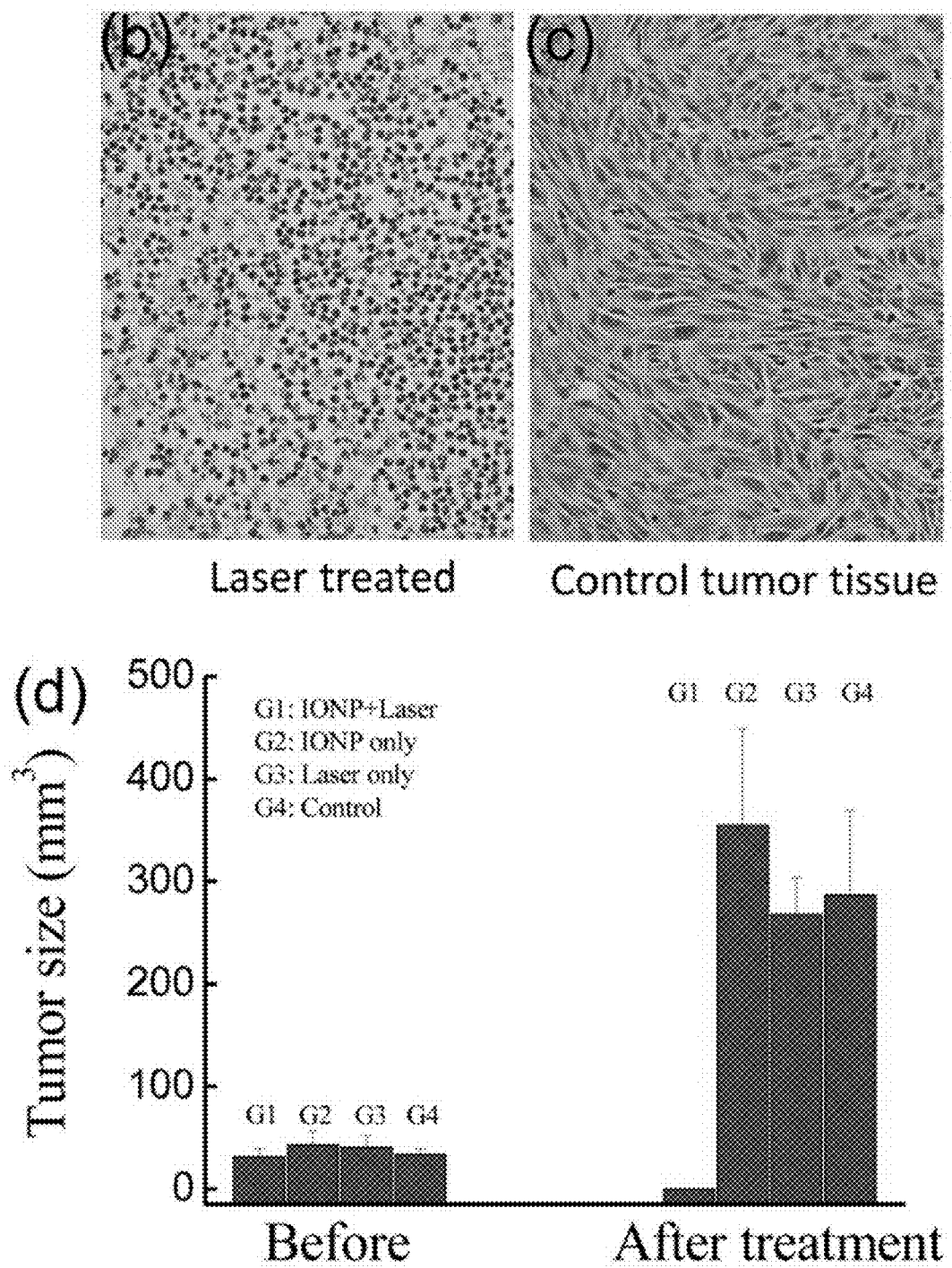

FIG. 4a shows representative photos of tumor-bearing mice after laser treatment. For the mice intravenously injected with HCIONPs tissue hemorrhaging was observed (top, left) right after laser irradiation for 10 minutes, revealing the damage of tumor blood vessels by the heated nanoparticles around them. Tumor regression is rapid, observable one day after laser illumination with complete tumor regression three weeks post irradiation (top, right). In marked contrast, for the control mice exposed to the laser but only injected with PBS, the tumor tissue does not have any obvious hemorrhaging after laser treatment (bottom, left). As expected, the tumor tissue grows quickly and becomes ulcerated after three weeks (bottom, right). Haematoxylin and eosin (H&E) stained tumor slices further reveal obvious necrosis of tumor tissue immediately following photothermal treatment for the mice injected with nanocrystals relative to control normal tumor tissue as shown in FIGS. 4b and 4c. Strikingly, all tumors on five nanocrystal-injected mice were ablated after one time laser irradiation without relapse over three months. Conversely, tumors of fifteen control mice in three control groups showed rapid tumor growth and led to animal death within one month as shown in FIG. 4d. This data clearly demonstrates that as-prepared HCIONPs (further coated with antibiofouling polymer coating) function as effective PTT agents.

Long Term Toxicity of Intravenously Administered HCIONPs

Figure 5A:
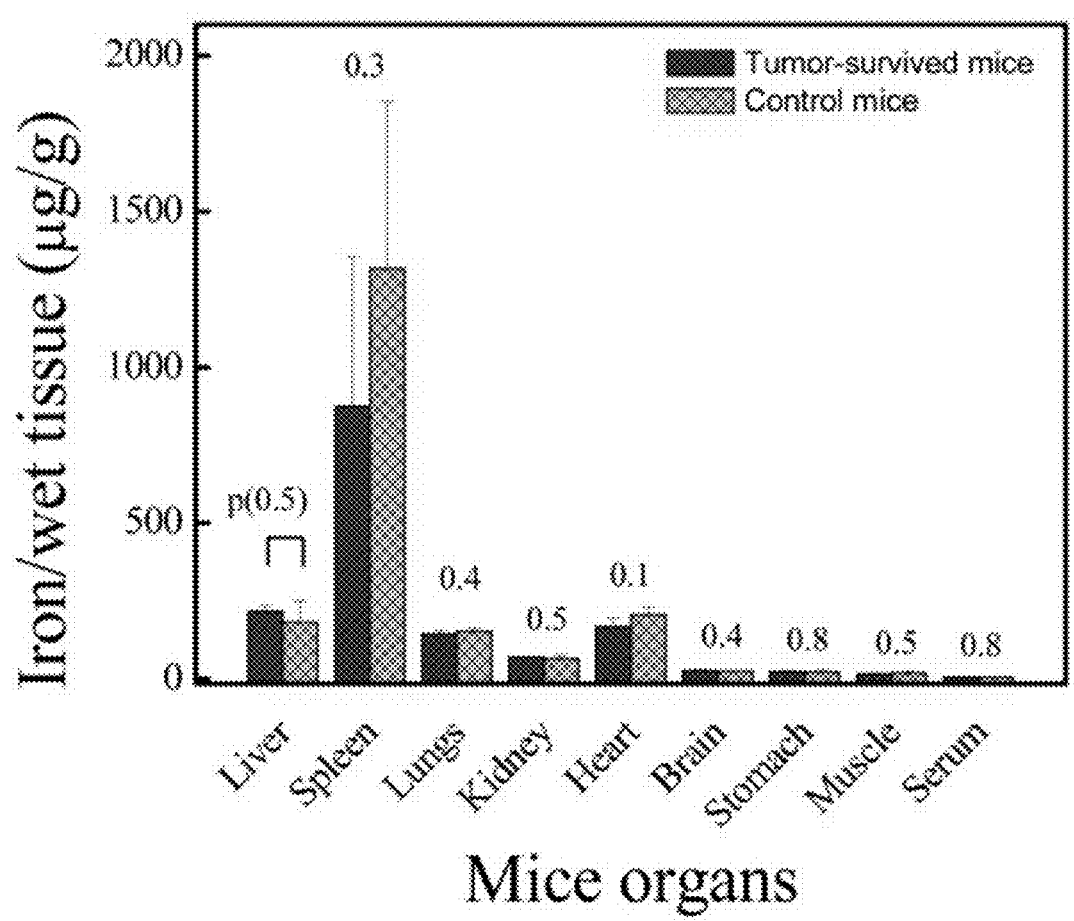
FIGS. 5a-e. (a) Biodistribution of magnetic nanocrystals in main organs 4 months after tail vein injection from tumor-survived mice after photothermal therapy. Numbers are p-value of iron content in each organ between two group mice. (b-e) H&E tissue staining of liver (b-c) and spleen (d-e) from tumor-survived (left) and control mouse (right).
Figure 5:
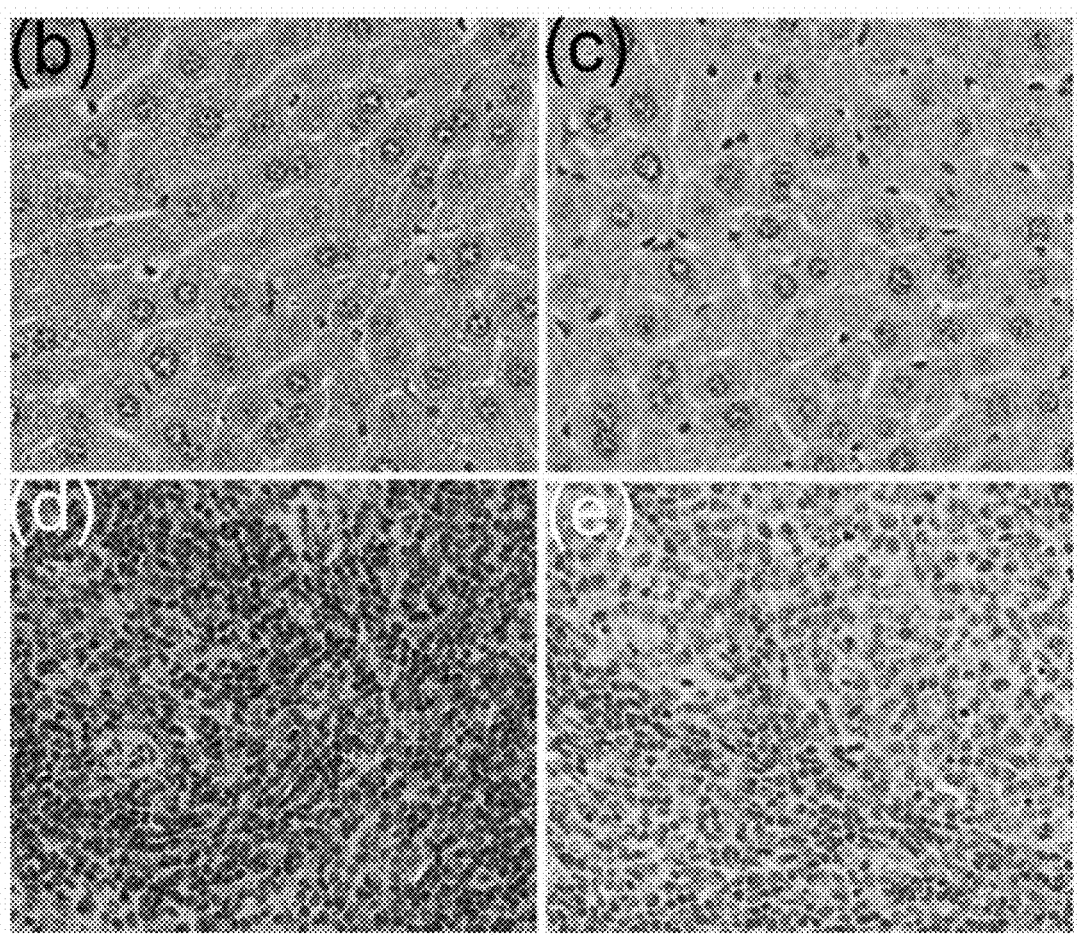
Figure 12:
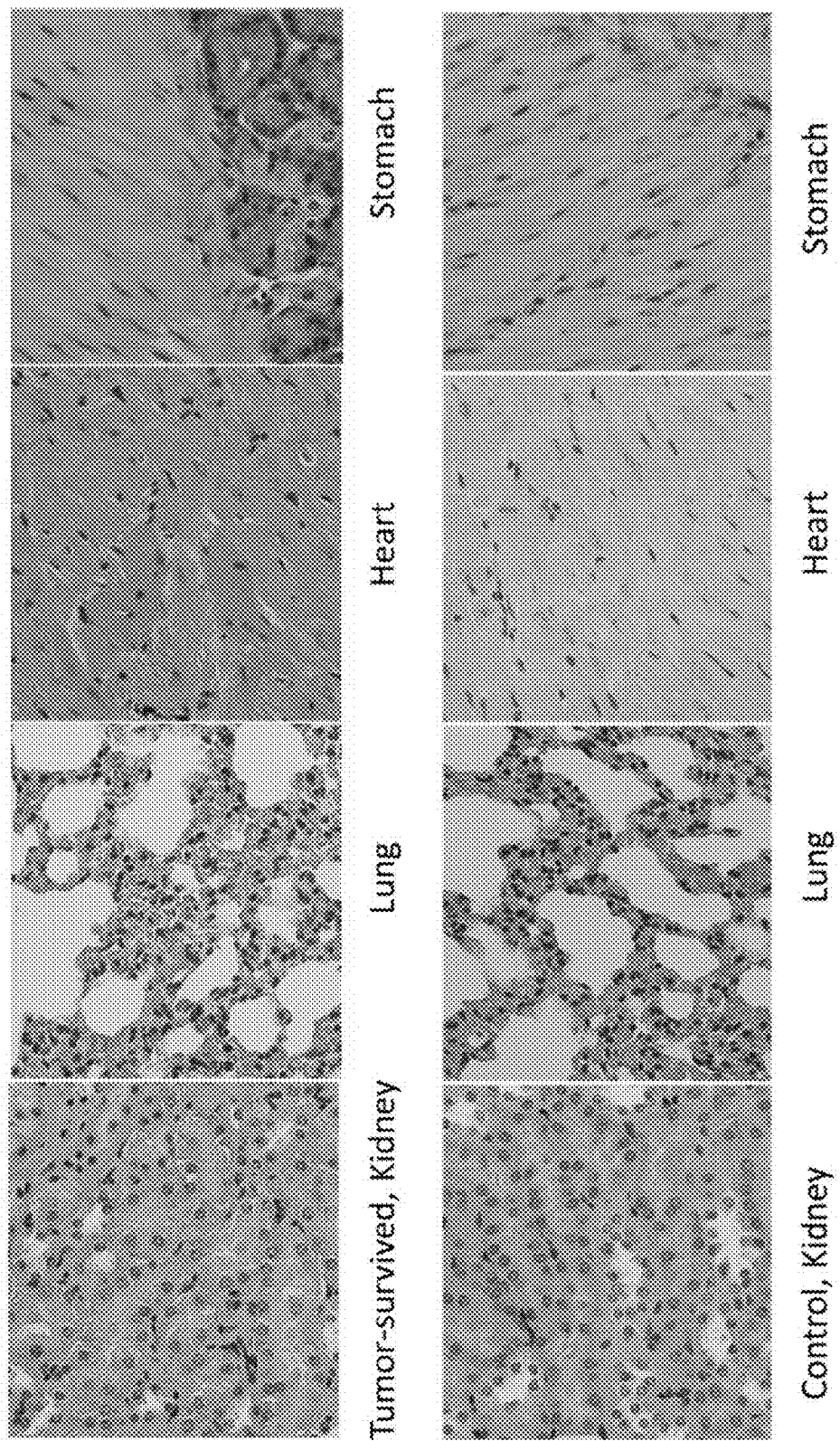
FIG. 12. H&E tissue staining of the rest main organs from tumor-survived and control mouse.

To assess the long term systemic exposure and potential toxicity of administered HCIONPs, ICP-OES was utilized to analyze the biodistribution of the magnetic nanocrystals for all the tumor-survived mice four month post treatment. The iron concentrations within all major organs were compared to control mice without injection of magnetic nanoparticles. As shown in FIG. 5a, organ iron concentrations were not significantly different between tumor-survived mice and control mice. This data reveals that the intravenously injected nanoparticles were gradually cleared from the body over time, as previously suggested through evidence of urinary excretion [42]. The long term toxicity is also evaluated by H&E tissue staining of the main organs as shown in FIGS. 5b-5e (also FIG. 12). This data suggests that there is no obvious tissue damage to tumor-survived mice compared to control treatment.

Effect of HCIONP Crystal Lattice Orientation on Photothermal Efficiency

Figure 6:
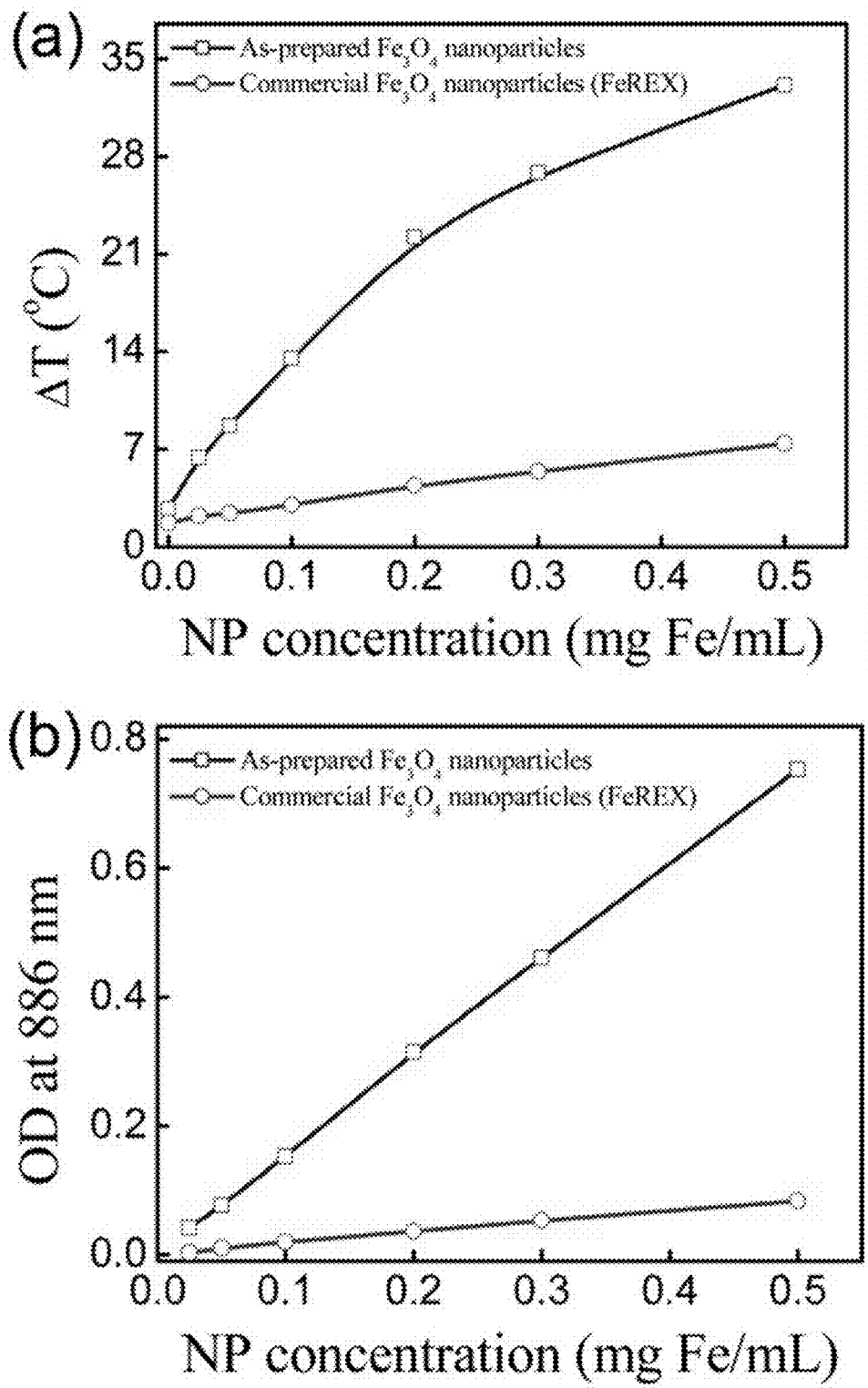
FIG. 6. (a) Measure temperature change of increasing concentrations of both as-prepared magnetic nanocrystals and commercial magnetic nanoparticles from FeREX (Bio-PAL) after laser irradiation for 10 min. (b) Optical density (OD) at 886 nm of both magnetic nanoparticles at different nanoparticle concentrations.
Figure 13:
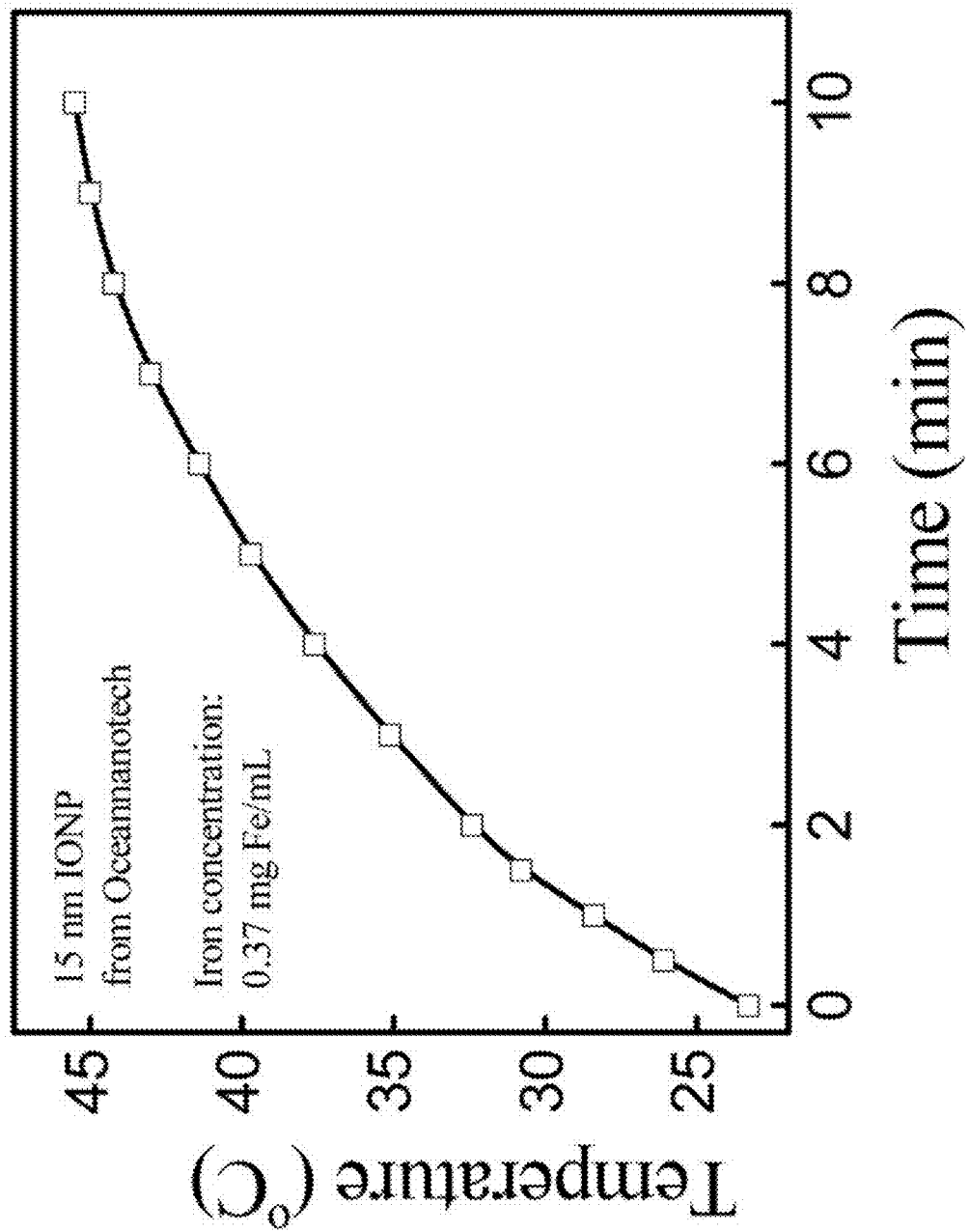
FIG. 13. Measured temperature of commercial 15-nm magnetic nanocrystals from Oceannanotech. All temperatures were measured during 10 minutes of illumination with a diode laser (λ=885 nm) at a fluence rate of 2.5 W/cm$^2$.
Figure 14:
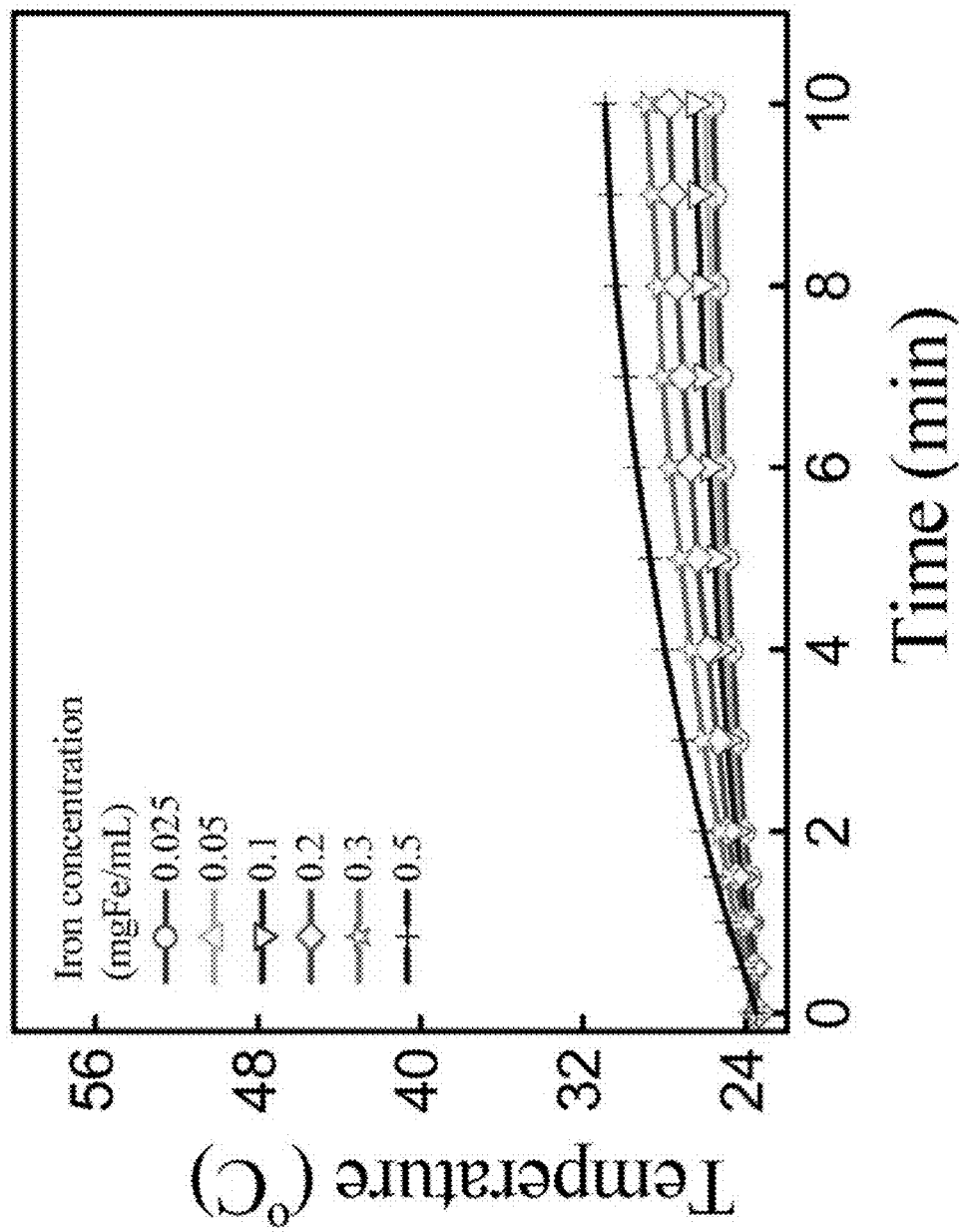
FIG. 14. Measured temperature of increasing concentrations of magnetic nanoparticles from FeREX in water. All temperatures were measured during 10 minutes of illumination with a diode laser (λ=885 nm) at a fluence rate of 2.5 W/cm$^2$.
Figure 15:
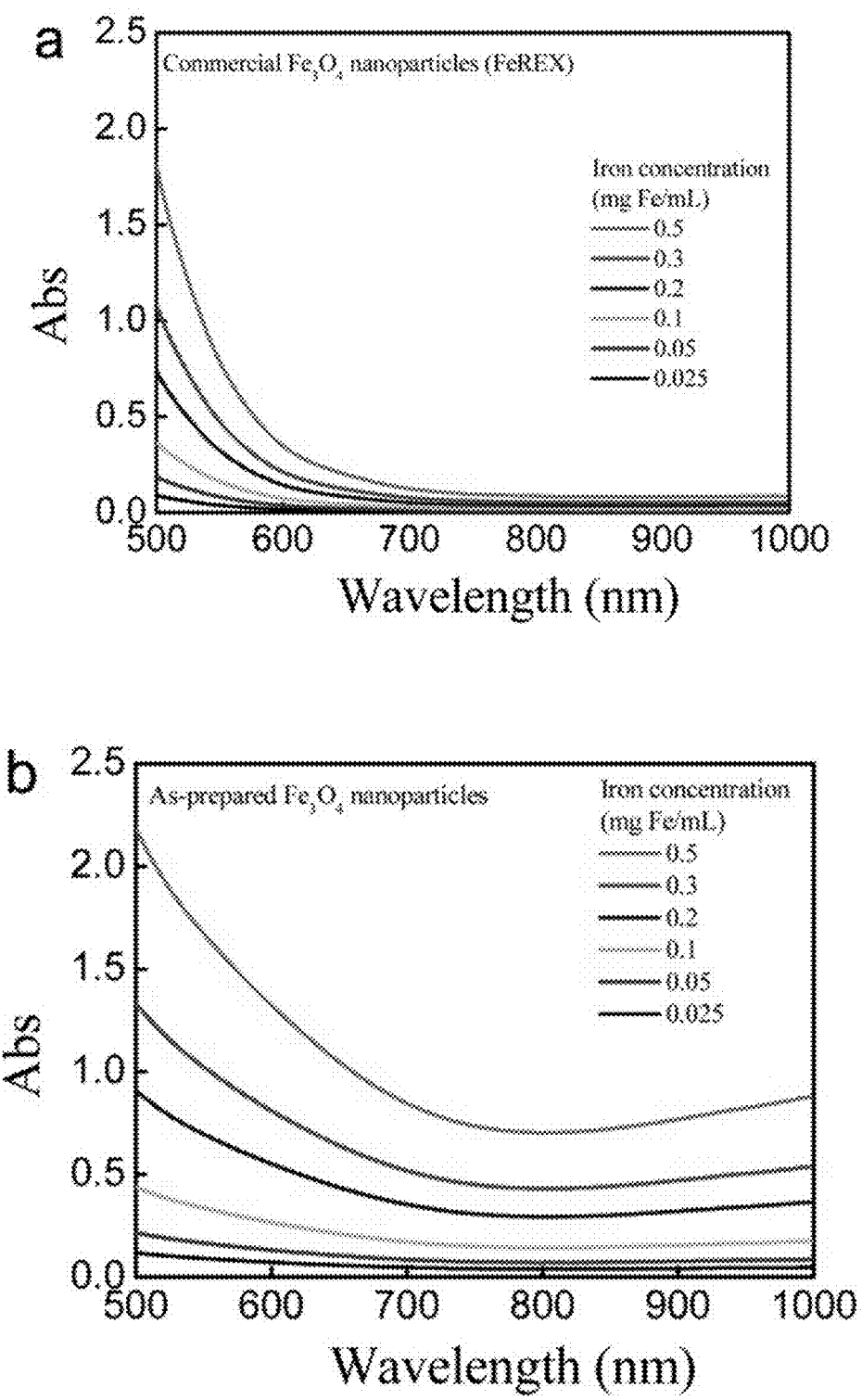
FIG. 15 (a) UV-vis-NIR absorbance spectra of commercial magnetic nanoparticles from FeREX (a) and as-prepared HCIONPs (b).

Since magnetic nanoparticles have been studied for many years, it is important to understand what makes the as-prepared HCIONPs unique from other magnetic nanoparticles as an effective photothermal mediator. Magnetic nanoparticles made by thermal decomposition (15 nm) from Oceannanotech were employed to select a different polymer coating from the one described above in order to rule out any contribution by the polymer coating (FIG. 13) [36]. The data shows a similar temperature profile, revealing that the photothermal effect has nothing to do with the polymer coating but rather the magnetic nanoparticle core. The as-prepared HCIONPs were then compared to another commercial magnetic nanomaterial from FeREX (BioPAL, Worcester, Mass.) which was made in aqueous solution[43]. After measuring the temperature profiles of FeREX under the same conditions, it was found that the temperature increase at an iron concentration of 0.5 mg Fe/mL was only 7.4° C., far less than the as-prepared HCIONPs as shown in FIG. 6a (also FIG. 14). UV-vis-NIR absorbance spectra reveal an obviously different absorption profile between the two magnetic nanomaterials (FIG. 15). As-prepared HCIONPs have obvious absorption over near infrared range, while the absorption for commercial magnetic nanoparticles from FeREX is negligible over the same range. Furthermore, FIG. 6b shows the optical density (OD) at 886 nm grows linearly with increasing concentration of both types of magnetic nanoparticles. For as-prepared HCIONPs, the OD linearly increases from 0.042 to 0.753 as the nanoparticle concentration increases from 0.025 to 0.5 mg Fe/mL. In contrast, for magnetic nanoparticles from FeREX the OD number at an iron concentration of 0.5 mg Fe/mL reaches a maximum of 0.083, nine times lower than the HCIONPs.

Figure 7:
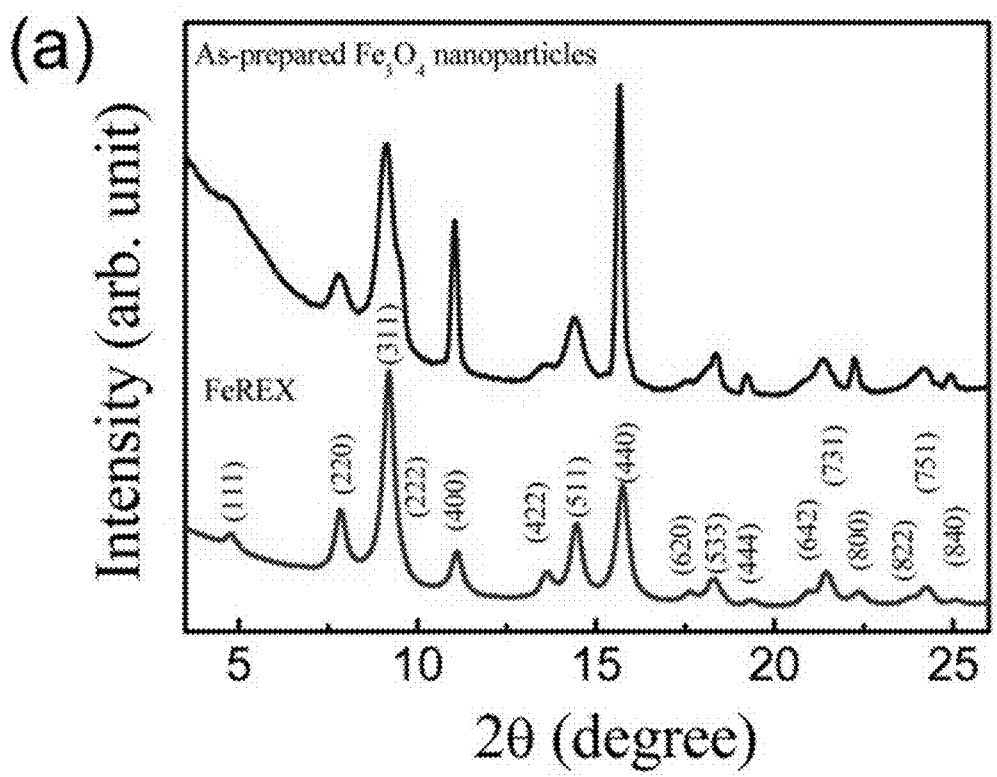
FIG. 7. (a) Synchrotron X-ray diffraction profile of as-prepared and commercial magnetic nanocrystals (FeREX). (b) Relative intensity of major diffraction peaks of both samples and standard crystals.
Figure 7:
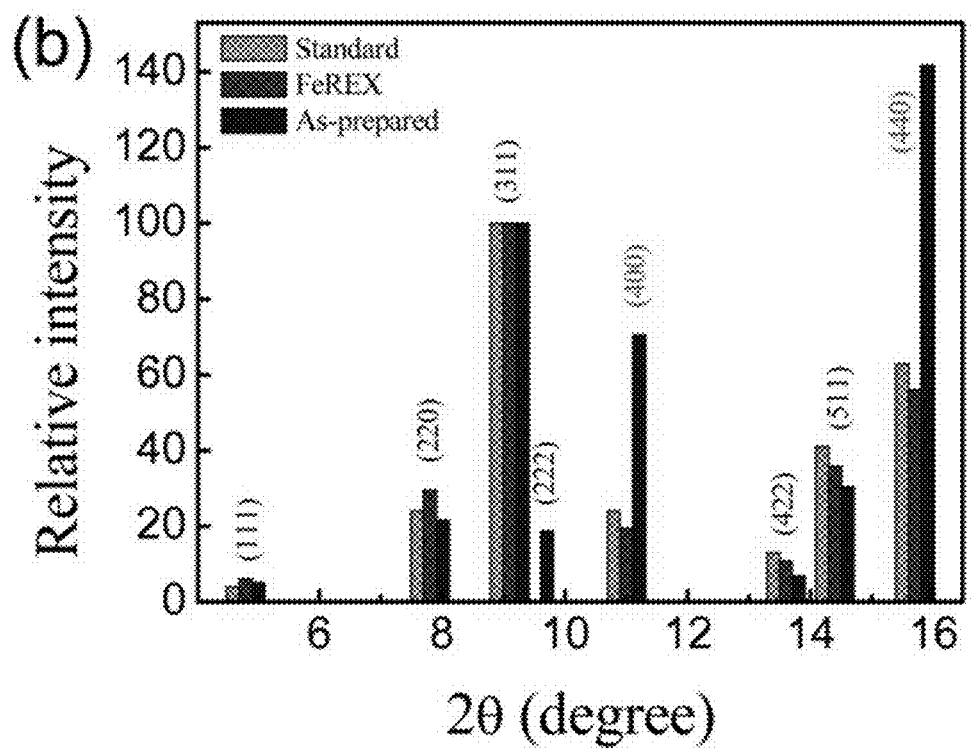
Figure 16:
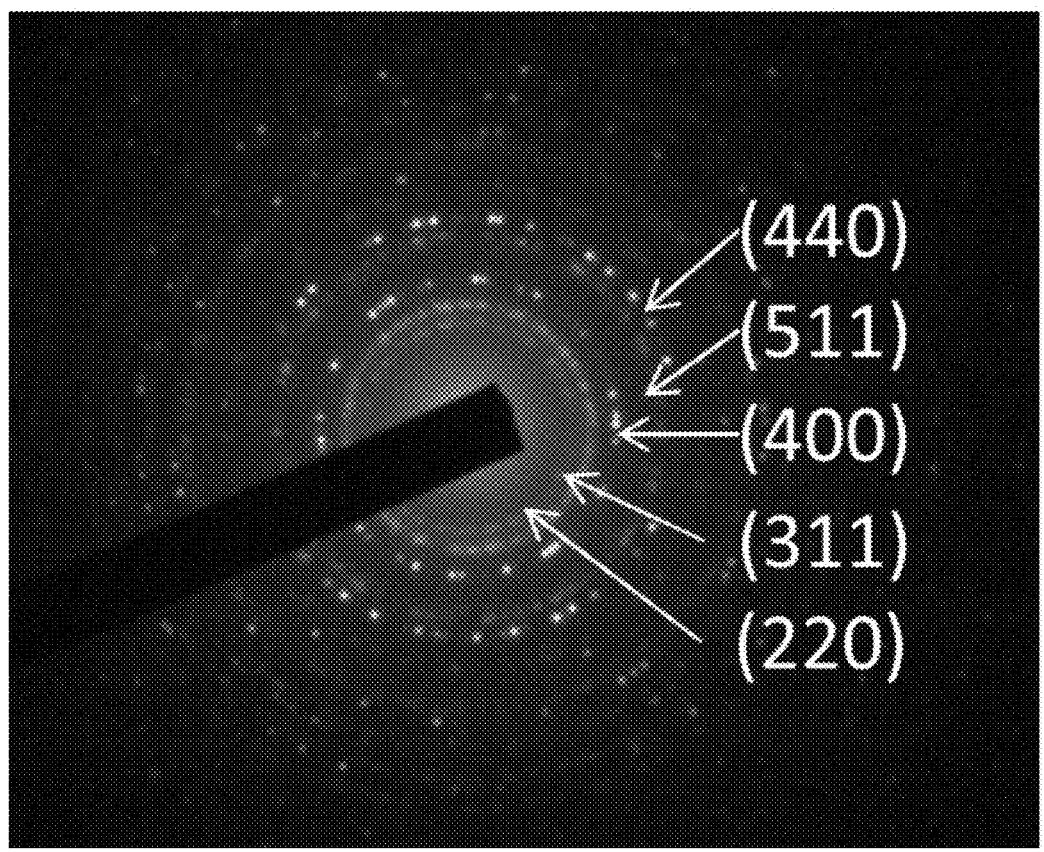
FIG. 16. Electron diffraction of as-prepared HCIONPs.
Figure 17:
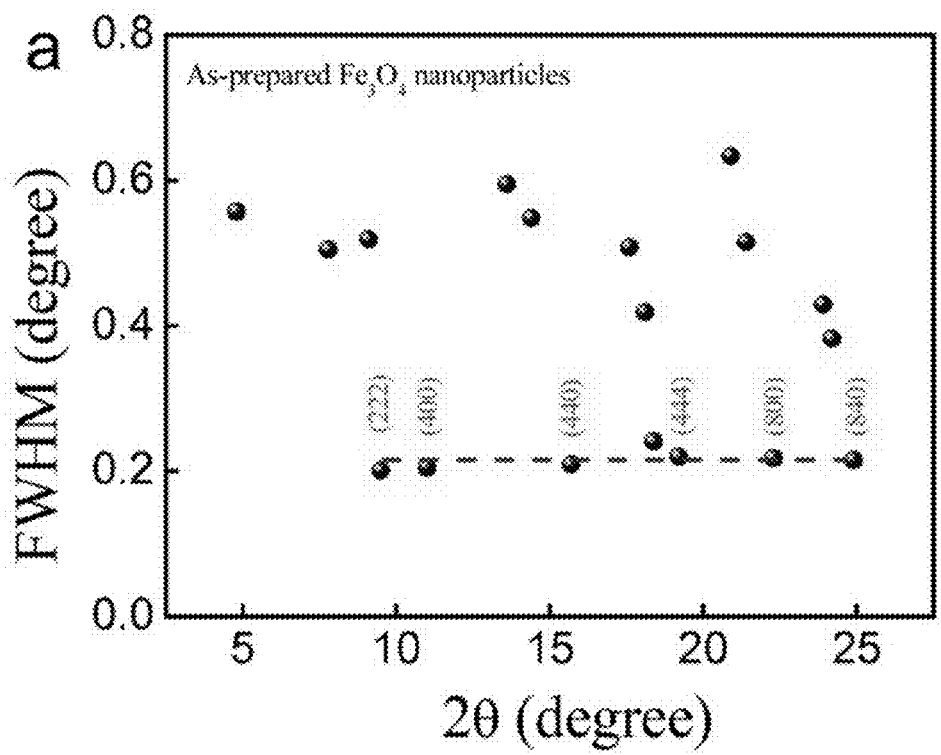
FIG. 17. Full width at half maximum (FWHM) (degree) of as-prepared HCIONPs (a) and nanoparticles from FeRex (b). The pink dotted line (left) indicates that all fourfold symmetry indexes have smaller FWHM than other indexes from the same sample. The black solid line (right) is the best linear fit of all the data points.
Figure 17:
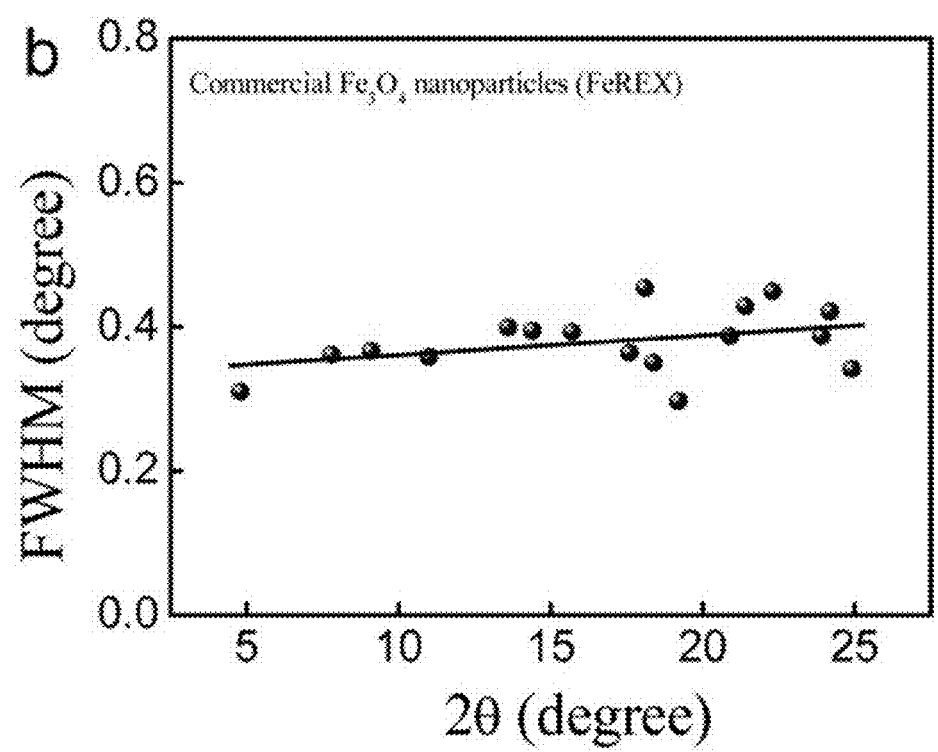
Figure 18:
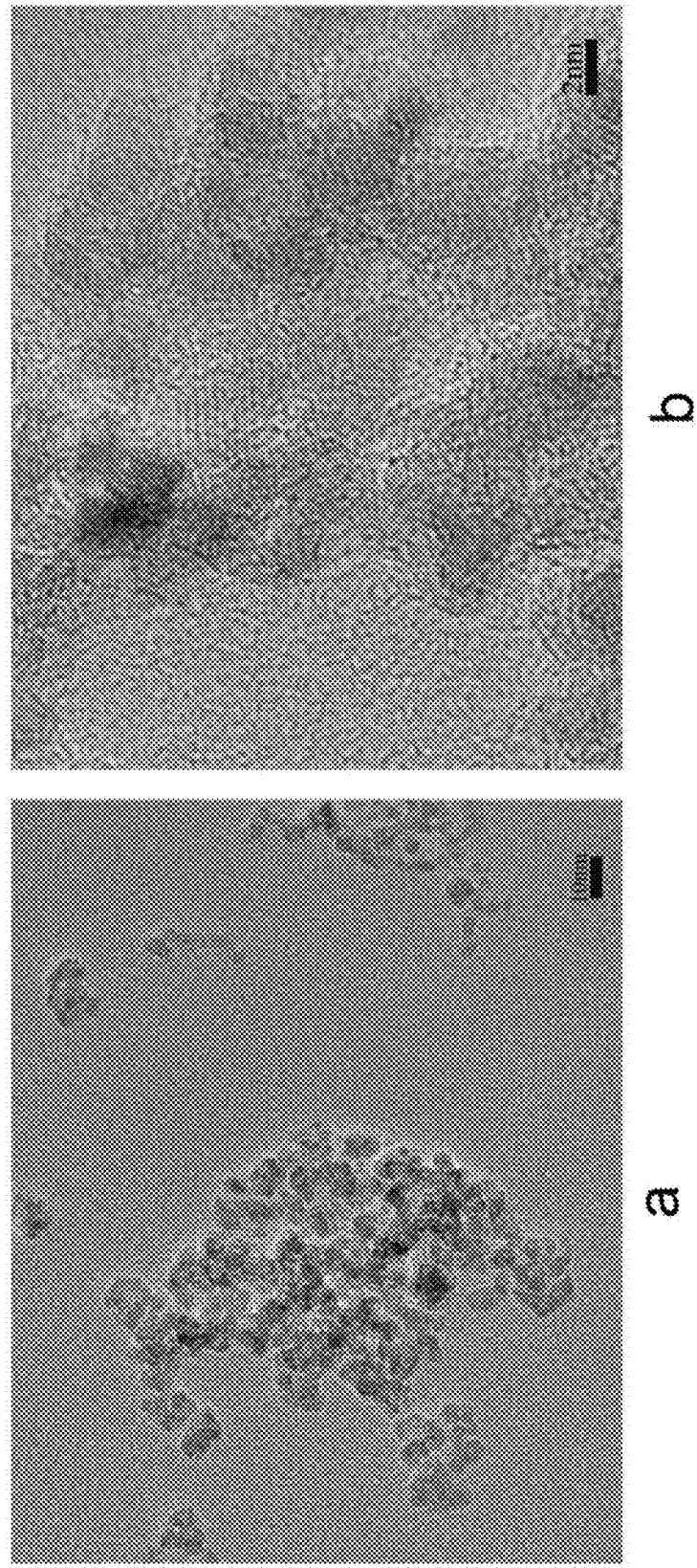
FIG. 18. (a) TEM image and (b) High-resolution TEM image of magnetic nanoparticles from FeRex
Figure 19:
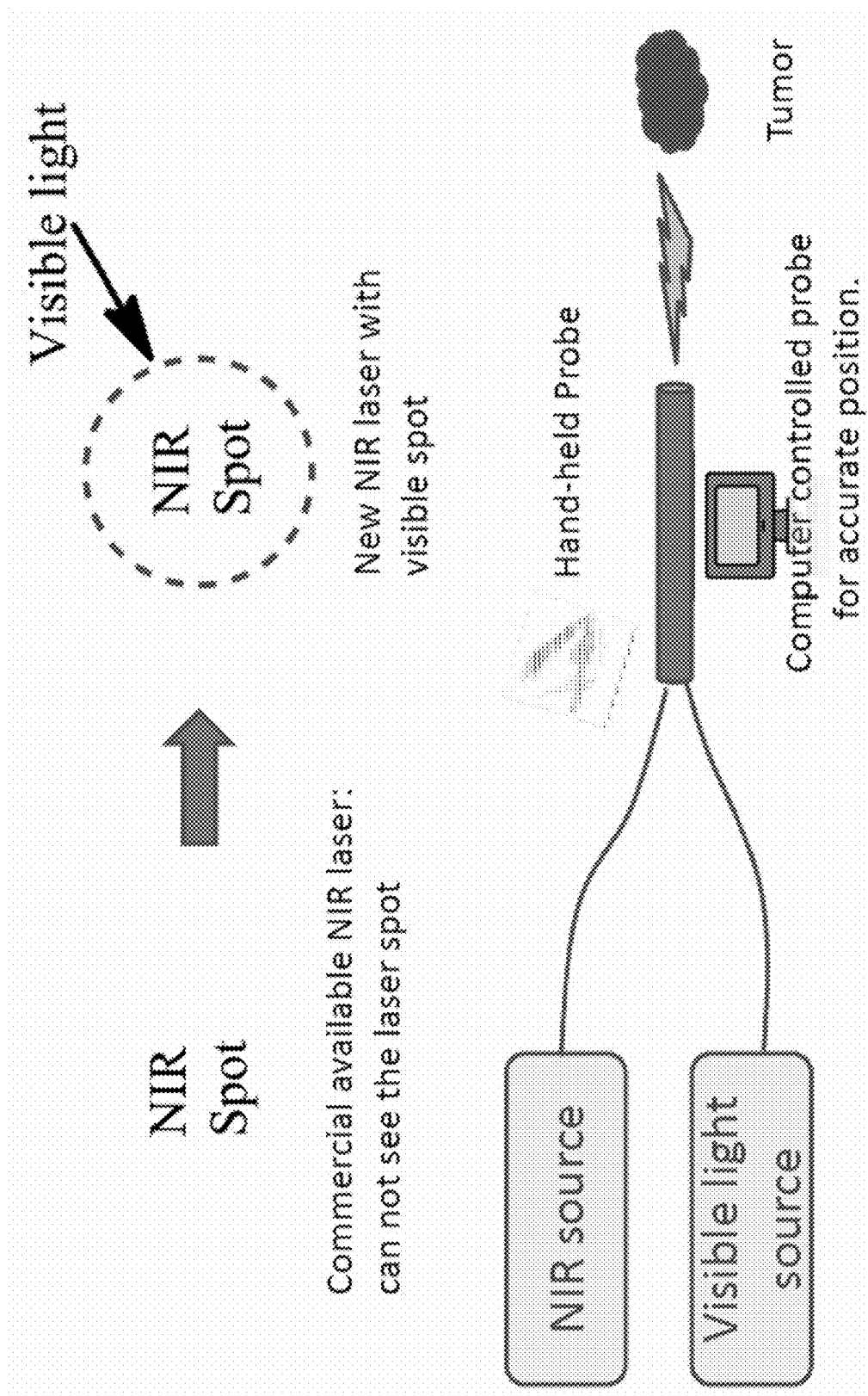
FIG. 19 shows one exemplary design of a NIR laser with visible light component to generate a visible spot where the NIR laser is shining on a subject.
Figure 20:
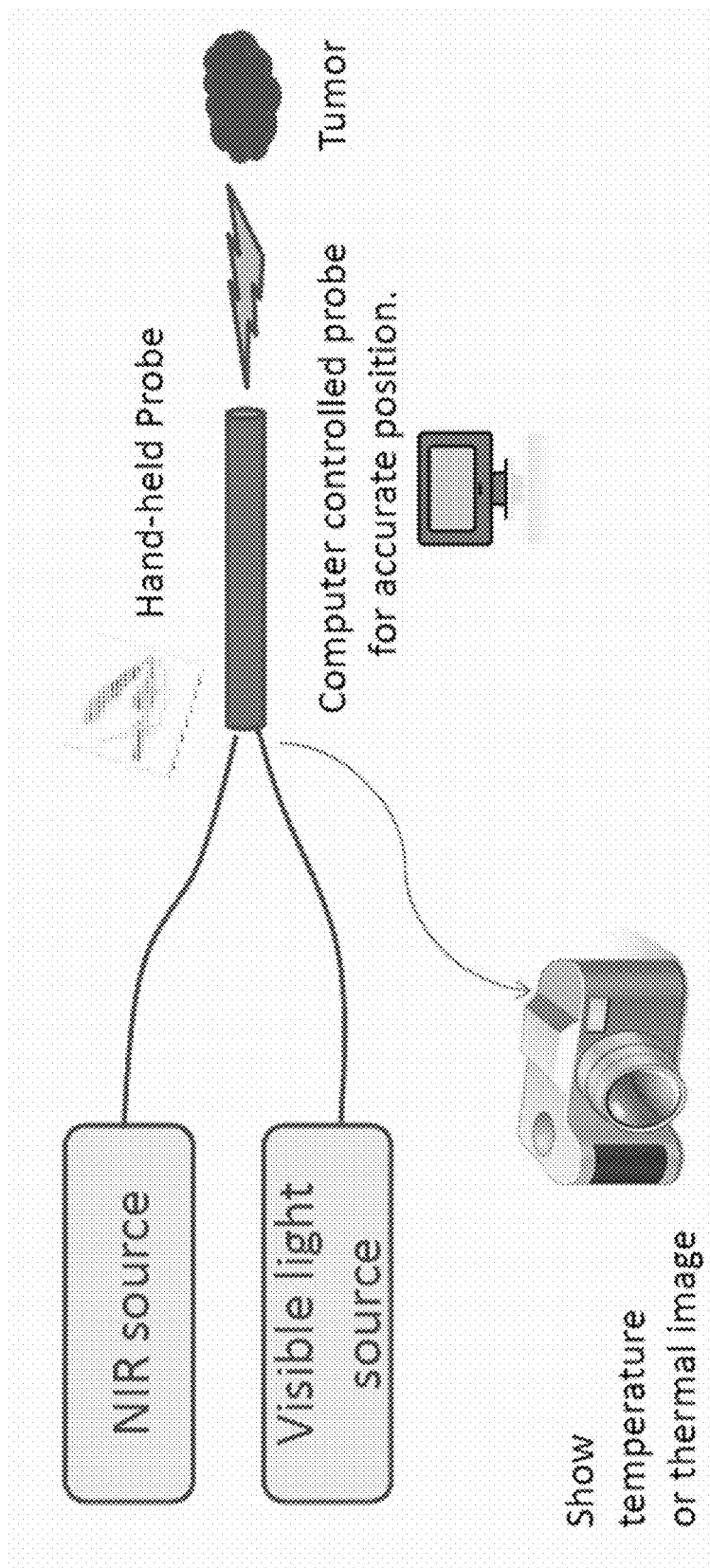
FIG. 20 shows one exemplary design of a NIR laser with the ability to show the real-time temperature profile, combined with an infrared camera.

To better understand the two magnetic nanoparticles' different photothermal effects, synchrotron X-ray diffraction (XRD) was used, which has a better signal-to-noise ratio for nanoparticles than lab-XRD, to further study the crystal structure of these two kind of magnetic nanoparticles as shown in FIG. 7. The observed XRD profiles of the two samples have exactly matched diffraction peaks, which suggest that they have the same crystal structure. Comparing to the standard JCPDS database, both as-prepared and commercial magnetic nanoparticles are Fe3O4. However, the as-prepared HCIONPs show strong anisotropic characters in the measured XRD profile because the intensity of the diffraction maxima of (400) and (440) are much stronger than expected values as shown in FIG. 7a. The relative intensities of diffraction peaks for the measured samples are shown in FIG. 7b together with the standard from the crystal database. The relative intensities of the commercial sample from FeREX show no obvious difference from the standard with the strongest diffraction of (311). However, (440) diffraction becomes the strongest peak in the as-prepared HCIONPs. This was also observed by their electron diffraction pattern, where (440) is the brightest diffraction ring (FIG. 16). The change of the relative intensity of diffraction peaks suggest that the as-prepared HCIONPs may have a preferred orientation character along the (100) and (110) lattice planes (i.e., (400) and (440) planes) [44]. This preferred plane orientation is also revealed by the change of full width at half maximum (FWHM) of each diffraction peak. Surprisingly, for as-prepared HCIONPs, the FWHM of diffraction peaks from both (400) and (440) becomes narrower than those from (311) and (511) from the same sample (FIG. 17a). Based on Scherrer's Formula [45], the narrower the FWHM is, the bigger the ordered lattice domain. In other words, the as-prepared HCIONPs have preferred lattice orientation along (400) and (440) planes. Although similar synthesis processes to make these HCIONPs have been reported, such a unique crystal character revealed by their distinguished XRD profile is probably caused by modification of the synthesis process. Recent work showed that iron oxide nanoparticles made by thermal decomposition with modified hot-injection method have a preferred plane orientation [44]. The preferred plane orientation may contribute to the effective absorption of infrared light for as-prepared HCIONPs to generate heat under a NIR light. In contrast, all the diffraction peaks of magnetic nanoparticles from FeREX show similar FWHM (Figure S17b). In addition, the TEM image shows that their core size is around 10 nm and the HRTEM image further reveals that these nanoparticles are poorly crystallized iron oxide nanoparticles, which are less organized as compared to as-prepared HCIONPs (FIG. 18). This study suggests that one may be able to improve magnetic nanoparticle's photothermal efficiency by optimizing the lattice orientation.

REFERENCES

1. Cherukuri P, Glazer E S, Curleya S A: Targeted hyperthermia using metal nanoparticles. Adv Drug Deliver Rev 62(3), 339-345 (2010).
2. Melancon M P, Zhou M, Li C: Cancer Theranostics with Near-Infrared Light-Activatable Multimodal Nanoparticles. Accounts Chem Res 44(10), 947-956 (2011).
3. Kennedy L C, Bickford L R, Lewinski N A et al.: A New Era for Cancer Treatment: Gold-Nanoparticle-Mediated Thermal Therapies. Small 7(2), 169-183 (2011).
4. Yang K, Feng L Z, Shi X Z, Liu Z: Nano-graphene in biomedicine: theranostic applications. Chem Soc Rev 42(2), 530-547 (2013).
5. Hirsch L R, Stafford R J, Bankson J A et al.: Nanoshell-mediated near-infrared thermal therapy of tumors under magnetic resonance guidance. P Natl Acad Sci USA 100(23), 13549-13554 (2003).
6. Ke H T, Wang J R, Dai Z F et al.: Gold-Nanoshelled Microcapsules: A Theranostic Agent for Ultrasound Contrast Imaging and Photothermal Therapy. Angew Chem Int Edit 50(13), 3017-3021 (2011).
7. Huang X, El-Sayed I H, Qian W, El-Sayed M A: Cancer cell imaging and photothermal therapy in the near-infrared region by using gold nanorods. J Am Chem Soc 128(6), 2115-2120 (2006).
8. Kuo W S, Chang C N, Chang Y T et al.: Gold Nanorods in Photodynamic Therapy, as Hyperthermia Agents, and in Near-Infrared Optical Imaging. Angew Chem Int Edit 49(15), 2711-2715 (2010).
9. Yavuz M S, Cheng Y Y, Chen J Y et al.: Gold nanocages covered by smart polymers for controlled release with near-infrared light. Nat Mater 8(12), 935-939 (2009).
10. Chen J Y, Glaus C, Laforest R et al.: Gold Nanocages as Photothermal Transducers for Cancer Treatment. Small 6(7), 811-817 (2010).
11. Ji X J, Shao R P, Elliott A M et al.: Bifunctional gold nanoshells with a superparamagnetic iron oxide-silica core suitable for both MR imaging and photothermal therapy. J Phys Chem C 111(17), 6245-6251 (2007).
12. Dong W J, Li Y S, Niu D C et al.: Facile Synthesis of Monodisperse Superparamagnetic Fe3O4 Core@hybrid@Au Shell Nanocomposite for Bimodal Imaging and Photothermal Therapy. Adv Mater 23(45), 5392-+(2011).
13. Yang K, Hu L L, Ma X X et al.: Multimodal Imaging Guided Photothermal Therapy using Functionalized Graphene Nanosheets Anchored with Magnetic Nanoparticles. Adv Mater 24(14), 1868-1872 (2012).
14. Melancon M P, Lu W, Zhong M et al.: Targeted multifunctional gold-based nanoshells for magnetic resonance-guided laser ablation of head and neck cancer. Biomaterials 32(30), 7600-7608 (2011).
15. Zhang Q, Ge J P, Goebl J, Hu Y X, Sun Y G, Yin Y D: Tailored Synthesis of Superparamagnetic Gold Nanoshells with Tunable Optical Properties. Adv Mater 22(17), 1905-+(2010).
16. Zhou C, Long M, Qin Y, Sun X, Zheng J: Luminescent gold nanoparticles with efficient renal clearance. Angew Chem Int Ed Engl 50(14), 3168-3172 (2011).
17. Link S, Wang Z L, El-Sayed M A: How does a gold nanorod melt? J Phys Chem B 104(33), 7867-7870 (2000).
18. Liu X W, Tao H Q, Yang K, Zhang S A, Lee S T, Liu Z A: Optimization of surface chemistry on single-walled carbon nanotubes for in vivo photothermal ablation of tumors. Biomaterials 32(1), 144-151 (2011).
19. Tian Q W, Tang M H, Sun Y G et al.: Hydrophilic Flower-Like CuS Superstructures as an Efficient 980 nm Laser-Driven Photothermal Agent for Ablation of Cancer Cells. Adv Mater 23(31), 3542-+(2011).
20. Rockenberger J, Scher E C, Alivisatos A P: A new nonhydrolytic single-precursor approach to surfactant-capped nanocrystals of transition metal oxides. J Am Chem Soc 121(49), 11595-11596 (1999).
21. Hyeon T, Lee S S, Park J, Chung Y, Bin Na H: Synthesis of highly crystalline and monodisperse maghemite nanocrystallites without a size-selection process. J Am Chem Soc 123(51), 12798-12801 (2001).
22. Cheon J W, Kang N J, Lee S M, Lee J H, Yoon J H, Oh S J: Shape evolution of single-crystalline iron oxide nanocrystals. J Am Chem Soc 126(7), 1950-1951 (2004).

23. Sun S H, Zeng H, Robinson D B et al.: Monodisperse MFe2O4 (M=Fe, Co, Mn) nanoparticles. J Am Chem Soc 126(1), 273-279 (2004).
24. Yu W W, Falkner J C, Yavuz C T, Colvin V L: Synthesis of monodisperse iron oxide nanocrystals by thermal decomposition of iron carboxylate salts. Chem Commun (20), 2306-2307 (2004).
25. Ma L L, Feldman M D, Tam J M et al.: Small Multifunctional Nanoclusters (Nanoroses) for Targeted Cellular Imaging and Therapy. Acs Nano 3(9), 2686-2696 (2009).
26. Lee N, Hyeon T: Designed synthesis of uniformly sized iron oxide nanoparticles for efficient magnetic resonance imaging contrast agents. Chem Soc Rev 41(7), 2575-2589 (2012).
27. Lammers T, Kiessling F, Hennink W E, Storm G: Nanotheranostics and Image-Guided Drug Delivery: Current Concepts and Future Directions. Mol Pharmaceut 7(6), 1899-1912 (2010).
28. Lee J H, Jang J T, Choi J S et al.: Exchange-coupled magnetic nanoparticles for efficient heat induction. Nat Nanotechnol 6(7), 418-422 (2011).
29. Shen S, Ren J F, Zhu X Y et al.: Monodisperse magnetites anchored onto carbon nanotubes: a platform for cell imaging, magnetic manipulation and enhanced photothermal treatment of tumors. J Mater Chem B 1(14), 1939-1946 (2013).
30. Liao M Y, Lai P S, Yu H P, Lin H P, Huang C C: Innovative ligand-assisted synthesis of NIR-activated iron oxide for cancer theranostics. Chem Commun 48(43), 5319-5321 (2012).
31. Chu M Q, Shao Y X, Peng J L et al.: Near-infrared laser light mediated cancer therapy by photothermal effect of Fe3O4 magnetic nanoparticles. Biomaterials 34(16), 4078-4088 (2013).
32. Chen H W, Wu X Y, Duan H W et al.: Biocompatible Polysiloxane-Containing Diblock Copolymer PEO-b-P gamma MPS for Coating Magnetic Nanoparticles. Acs Appl Mater Inter 1(10), 2134-2140 (2009).
33. Lee H, Lee E, Kim D K, Jang N K, Jeong Y Y, Jon S: Antibiofouling polymer-coated superparamagnetic iron oxide nanoparticles as potential magnetic resonance contrast agents for in vivo cancer imaging. J Am Chem Soc 128(22), 7383-7389 (2006).
34. Kang Y S, Risbud S, Rabolt J F, Stroeve P: Synthesis and characterization of nanometer-size Fe3O4 and gamma-Fe2O3 particles. Chem Mater 8(9), 2209-& (1996).
35. Xie J, Xu C, Kohler N, Hou Y, Sun S: Controlled PEGylation of monodisperse Fe3O4 nanoparticles for reduced non-specific uptake by macrophage cells. Adv Mater 19(20), 3163-+(2007).
36. Chen H W, Wang L Y, Yeh J et al.: Reducing non-specific binding and uptake of nanoparticles and improving cell targeting with an antifouling PEO-b-P gamma MPS copolymer coating. Biomaterials 31(20), 5397-5407 (2010).
37. Cabral H, Matsumoto Y, Mizuno K et al.: Accumulation of sub-100 nm polymeric micelles in poorly permeable tumours depends on size. Nat Nanotechnol 6(12), 815-823 (2011).
38. Zha Z B, Yue X L, Ren Q S, Dai Z F: Uniform Polypyrrole Nanoparticles with High Photothermal Conversion Efficiency for Photothermal Ablation of Cancer Cells. Adv Mater 25(5), 777-782 (2013).
39. Huang X H, Peng X H, Wang Y Q et al.: A Reexamination of Active and Passive Tumor Targeting by Using Rod-Shaped Gold Nanocrystals and Covalently Conjugated Peptide Ligands. Acs Nano 4(10), 5887-5896 (2010).
40. Gu L, Vardarajan V, Koymen A R, Mohanty S K: Magnetic-field-assisted photothermal therapy of cancer cells using Fe-doped carbon nanoparticles. J Biomed Opt 17(1), (2012).
41. Habash R W, Bansal R, Krewski D, Alhafid H T: Thermal therapy, part 1: an introduction to thermal therapy. Crit Rev Biomed Eng 34(6), 459-489 (2006).
42. Chou S W, Shau Y H, Wu P C, Yang Y S, Shieh D B, Chen C C: In Vitro and in Vivo Studies of FePt Nanoparticles for Dual Modal C T/MRI Molecular Imaging. J Am Chem Soc 132(38), 13270-13278 (2010).
43. Tassa C, Shaw S Y, Weissleder R: Dextran-Coated Iron Oxide Nanoparticles: A Versatile Platform for Targeted Molecular Imaging, Molecular Diagnostics, and Therapy. Accounts Chem Res 44(10), 842-852 (2011).
44. Ho C H, Tsai C P, Chung C C et al.: Shape-Controlled Growth and Shape-Dependent Cation Site Occupancy of Monodisperse Fe3O4 Nanoparticles. Chem Mater 23(7), 1753-1760 (2011).
45. Patterson A L: The Scherrer formula for x-ray particle size determination. Phys Rev 56(10), 978-982 (1939).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating at least one tumor in a subject comprising:
   a) treating a subject with a composition comprising photothermal nanoparticles,
      wherein said subject comprises at least one tumor,
      wherein said photothermal nanoparticles individually comprise a biocompatible coating surrounding a highly crystallized $Fe_3O_4$ core,
      wherein said highly crystallized $Fe_3O_4$ core of said photothermal nanoparticles has an X-ray diffraction (XRD) pattern where the brightest diffraction ring is from the 440 plane, and
      wherein said treating is under conditions such that at least a portion of said photothermal nanoparticles infiltrate said at least one tumor; and
   b) subjecting said subject to photothermal therapy:
      i) on the first day of a three week period, and
      ii) on no more than three additional days of said three week period,
      wherein said photothermal therapy: A) comprises the use of a device that emits electromagnetic radiation with a wavelength between about 865 nm and 1000 nm, and B) causes said at least one tumor to be reduced in size or become undetectable at the end of said three week period.

2. The method of claim 1, wherein said highly crystallized $Fe_3O_4$ core of said photothermal nanoparticles has a preferred lattice orientation along the 400 and 440 XRD diffraction planes.

3. The method of claim 1, wherein said subject is subjected to said photothermal therapy on no more than two additional days of said three week period.

4. The method of claim 1, wherein said subject is subjected to said photothermal therapy one no more than one additional day of said three week period.

5. The method of claim 1, wherein said subject is subjected to said photothemal therapy on only said first day of said three week period.

6. The method of claim 1, wherein said photothermal therapy causes said at least one tumor to be reduced in size at least 50% at the end of said three week period.

7. The method of claim 1, wherein said treating comprises administering said photothermal nanoparticles to said subject intravenously.

8. The method of claim 1, herein said photothermal nanoparticles have a size between 18 nm and 30 nm.

9. The method of claim 1, wherein said biocompatible coating comprises a polysiloxane-containing amphiphilic copolymer.

10. The method of claim 1, wherein said device comprises a laser and/or LED.

11. The method of claim 1, wherein the length of treatment on said first day, and on any of said three additional days is between 5 and 15 minutes.

12. The method of claim 1, wherein said device further comprises a visible light source, wherein said visible light source allows a user to determine where said electromagnetic radiation is contacting said subject.

13. The method of claim 1, wherein said device further comprises a component that reveals the temperature of said subject's skin.

14. A method of treating cancer in a subject comprising:
a) treating a subject with a composition comprising photothermal nanoparticles,
wherein said subject comprises at plurality of cancer cells,
wherein said photothermal nanoparticles individually comprise a biocompatible coating surrounding a highly crystallized $Fe_3O_4$ core,
wherein said highly crystallized $Fe_3O_4$ core of said photothermal nanoparticles has an X-ray diffraction (XRD) pattern where the brightest diffraction ring is from the 440 plane, and
wherein said treating generates a plurality of photothermal nanoparticle-impregnated cancer cells in said subject; and
b) subjecting said subject to photothermal therapy using a device that emits electromagnetic radiation with a wavelength between about 865 nm and 1000 nm such that at least a portion of said photothermal nanoparticle-impregnated cancer cells are damaged or killed.

15. A system comprising:
a) a composition comprising photothermal nanoparticles, wherein said photothermal nanoparticles individually comprise a biocompatible coating surrounding a highly crystallized $Fe_3O_4$ core, and wherein said highly crystallized $Fe_3O_4$ core has an X-ray diffraction (XRD) pattern where the brightest diffraction ring is from the 440 plane; and
b) a device configured to emit electromagnetic radiation at least in the wavelengths between about 650 nm and 1000 nm.

16. The system of claim 15, wherein said highly crystallized $Fe_3O_4$ core of said photothermal nanoparticles has a preferred lattice orientation along the 400 and 440 XRD diffraction planes.

17. The system of claim 15, wherein said photothermal nanoparticles have a size between 18 nm and 30 nm.

18. The system of claim 15, wherein said device is configured to emit electromagnetic radiation with a wavelength between about 865 nm and 1000 nm.

19. The system of claim 15, wherein said device comprises a laser and/or LED.

20. The system of claim 15, wherein said biocompatible coating comprises a polysiloxane-containing amphiphilic copolymer.

* * * * *